United States Patent
Huang

(10) Patent No.: US 9,133,160 B2
(45) Date of Patent: Sep. 15, 2015

(54) SUBSTITUTED BENZIMIDAZOLE AND IMIDAZOPYRIDINE COMPOUNDS USEFUL AS CYP17 MODULATORS

(75) Inventor: Audris Huang, New Hope, PA (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 0 days.

(21) Appl. No.: 13/876,646

(22) PCT Filed: Sep. 23, 2011

(86) PCT No.: PCT/US2011/052984
§ 371 (c)(1),
(2), (4) Date: Mar. 28, 2013

(87) PCT Pub. No.: WO2012/044537
PCT Pub. Date: Apr. 5, 2012

(65) Prior Publication Data
US 2013/0310393 A1 Nov. 21, 2013

Related U.S. Application Data

(60) Provisional application No. 61/388,837, filed on Oct. 1, 2010.

(51) Int. Cl.
| | | |
|---|---|---|
| *C07D 401/04* | (2006.01) | |
| *C07D 471/04* | (2006.01) | |
| *C07D 403/04* | (2006.01) | |
| *C07D 401/14* | (2006.01) | |
| *C07D 417/14* | (2006.01) | |

(52) U.S. Cl.
CPC ............ *C07D 401/04* (2013.01); *C07D 401/14* (2013.01); *C07D 403/04* (2013.01); *C07D 417/14* (2013.01); *C07D 471/04* (2013.01)

(58) Field of Classification Search
USPC ............... 514/252.03, 338, 333, 255.05, 256, 514/313, 269, 307, 303; 544/405, 238, 322, 544/328, 333; 546/273.4, 256, 270.7, 162, 546/270.1, 144, 118
See application file for complete search history.

(56) References Cited

U.S. PATENT DOCUMENTS

| | | |
|---|---|---|
| 6,124,463 A | 9/2000 | Beck et al. |
| 6,303,600 B1 | 10/2001 | Cox et al. |
| 6,362,180 B1 | 3/2002 | Wilde et al. |
| 7,582,761 B2 | 9/2009 | Balan et al. |
| 2004/0236110 A1 | 11/2004 | Ladouceur et al. |
| 2006/0183911 A1 | 8/2006 | Charrier et al. |
| 2008/0255085 A1 | 10/2008 | Arvidsson et al. |
| 2009/0221591 A1 | 9/2009 | Hartmann et al. |
| 2013/0045980 A1 | 2/2013 | Velaparthi et al. |

FOREIGN PATENT DOCUMENTS

| | | |
|---|---|---|
| WO | WO00/01675 | 1/2000 |
| WO | WO2008/070354 | 6/2008 |
| WO | WO2008/075109 | 6/2008 |
| WO | WO2012/009510 | 1/2012 |
| WO | WO2012/064815 | 5/2012 |
| WO | WO2013/049263 | 4/2013 |

OTHER PUBLICATIONS

Arvanitis (CRF Ligands Via Suzuki and Negishi Couplings of 3-Pyridyl Boronic Acids or Halides with 2-Benzyloxy-4-chloro-3-nitrophyridine, Boorganic & Medicinal Chemistry Letters 13 (2003) pp. 289-291).*

Pinto-Bazurco Mendieta, M.A.E.., "Synthesis, biological evaluation and molecular modelling studies of novel ACD- and ABD-ring steroidomimetics as inhibitors of CYP17," Bioorganics & Medical Chemistry Letters, 18 (2008), pp. 267-273.

* cited by examiner

*Primary Examiner* — Kathrien Cruz
(74) *Attorney, Agent, or Firm* — Gary D. Greenblatt

(57) ABSTRACT

Disclosed are heteroaryl compounds of Formula (I), (I), or pharmaceutically acceptable salts thereof, wherein Z is CH or N; W is CR³ or N; and R¹, R², and R³ are defined herein. Also disclosed are methods of using such compounds in the treatment of at least one CYP17 associated condition, such as, for example, cancer, and pharmaceutical compositions comprising such compounds.

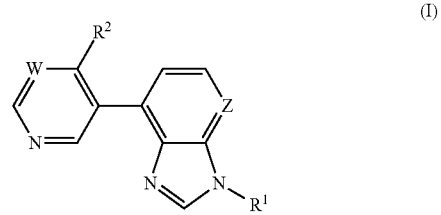

6 Claims, 1 Drawing Sheet

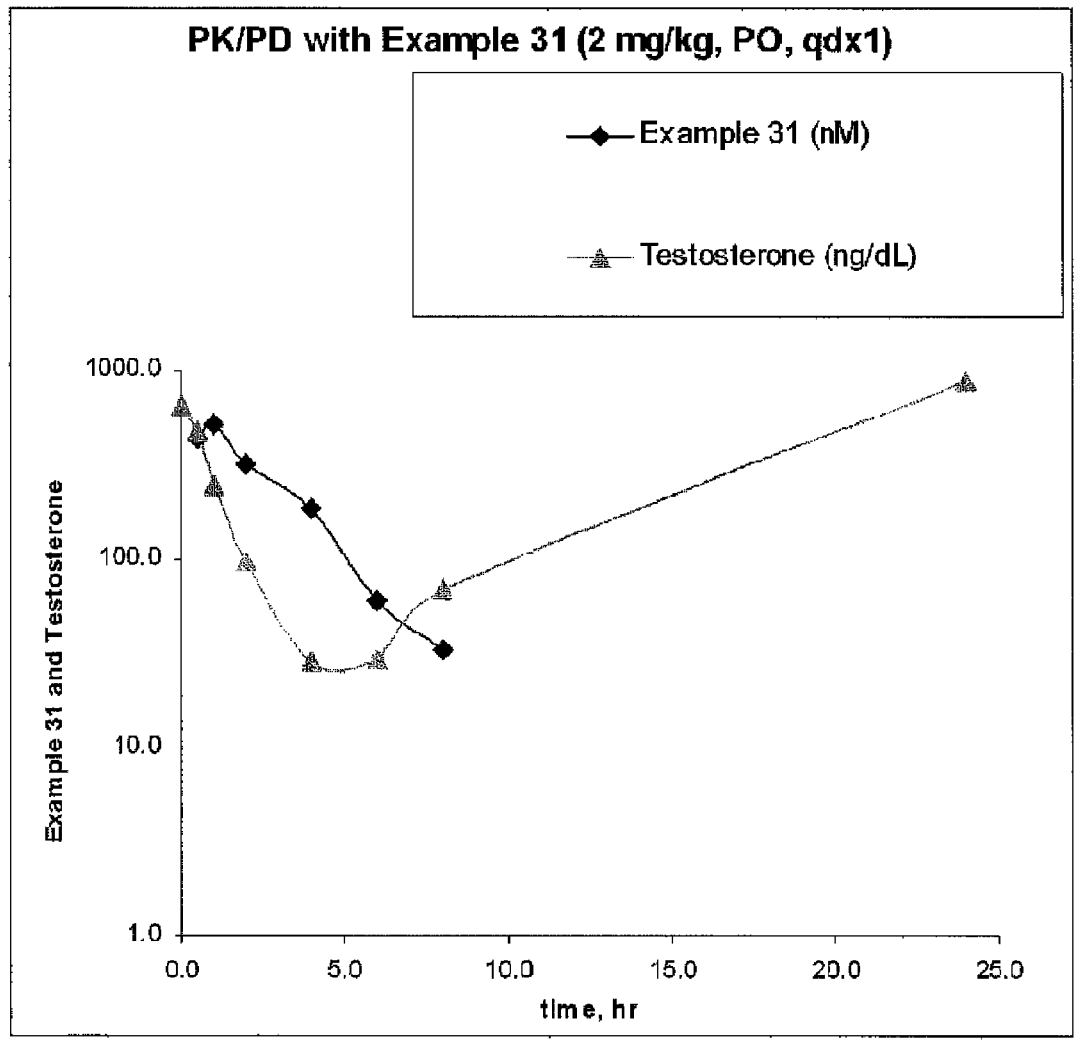

SUBSTITUTED BENZIMIDAZOLE AND IMIDAZOPYRIDINE COMPOUNDS USEFUL AS CYP17 MODULATORS

The present invention generally relates to substituted benzimidazole and imidazopyridine compounds useful as CYP17 inhibitors. Provided herein are substituted benzimidazole and imidazopyridine compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with anti-androgens more difficult.

The cytochrome P450 CYP17 is responsible for the biosynthesis of both dihydroepiandrostenedione and androstenedione which are precursors of both androgens and estrogen. Thus the production of all androgens and estrogens produced in the human body is mediated by CYP17. Blocking this enzyme would inhibit the production of gonadal, adrenal and tumoral androgens and could offer a new treatment option for prostate cancer and estrogen receptor-positive breast cancer patients.

Clinical proof-of-concept for CYP17 as a target for prostate cancer has been achieved with the antifungal ketoconazole and the steroidal CYP17 inhibitor abiraterone, which has progressed to Phase III clinical trials for prostate cancer.

There remains a need for compounds that are useful as inhibitors of CYP17 enzymes.

Applicants have found potent compounds that have activity as CYP17 inhibitors. These compounds are provided to be useful as pharmaceuticals with desired stability, bioavailability, therapeutic index, and toxicity values that are important to their drugability.

SUMMARY OF THE INVENTION

The present invention fills the foregoing need by providing substituted benzimidazole and imidazopyridine compounds of Formula (I), which are useful as inhibitors of CYP17 enzymes, including salts and prodrugs thereof.

The present invention also provides pharmaceutical compositions comprising a pharmaceutically acceptable carrier; and at least one compound of Formula (I), or salts or prodrugs thereof.

The present invention also provides a method of treating a disease or disorder associated with the activity of the CYP17 enzyme, the method comprising administering to a mammalian patient a compound of Formula (I), or pharmaceutically acceptable salts or prodrugs thereof.

The present invention also provides processes and intermediates for making the compounds of Formula (I), or salts or prodrugs thereof.

The present invention also provides the compounds of Formula (I), or pharmaceutically acceptable salts or prodrugs thereof, for use in therapy.

The present invention also provides use of a compound of Formula (I) or pharmaceutically acceptable salts or prodrugs thereof, for the manufacture of a medicament for the treatment of cancer.

The compounds of Formula (I) and compositions comprising the compounds are inhibitors of CYP17 enzymes, and may be used in treating, prevention, or curing various CYP17 enzyme related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawing described below.

FIG. 1 shows the plasma pharmacokinetics of Example 31 and plasma levels of testosterone in cynomolgus monkeys. Example 31 was formulated in 80% PEG-400/water at a volume of 1 mL/kg of monkey and administered orally at 2 mg/kg. The formulation was then dosed orally at time=0 hours and blood samples were taken over a 24 hour period to monitor for drug exposure and testosterone levels. (♦) Example 31 (nM); (▲) testosterone (ng/dL).

DETAILED DESCRIPTION

The first aspect of the invention provides substituted benzimidazole and imidazopyridine compounds of Formula (I):

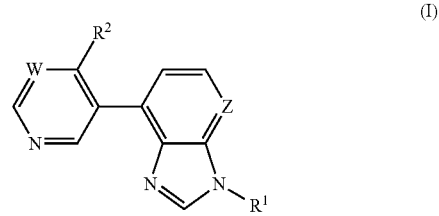

(I)

pharmaceutically acceptable salts or prodrugs thereof, wherein:

Z is CH or N;
W is $CR^3$ or N;
$R^1$ is:
  (i) $C_{1-6}$alkyl substituted with zero to 4 $R^a$;
  (ii) $C_{3-6}$ cycloalkyl substituted with zero to 4 $R^a$;
  (iii) —S(O)$_2$($C_{1-4}$alkyl), —S(O)$_2$($C_{1-4}$fluoroalkyl), or —C(O)($C_{1-6}$alkyl);
  (iv) aryl substituted with zero to 6 $R^b$;
  (v) heterocyclyl substituted with zero to 6 $R^c$; or
  (vi) heteroaryl substituted with zero to 6 $R^c$;
$R^2$ is:
  (i) H, halo, —CN, —$OR^d$, —$NR^eR^e$, or —C(O)$OR^f$;
  (ii) $C_{1-6}$alkyl substituted with zero to 4 $R^a$;
  (iii) $C_{3-6}$ cycloalkyl substituted with zero to 4 $R^a$;
  (iv) aryl substituted with zero to 6 $R^b$;
  (v) heterocyclyl substituted with zero to 6 $R^c$; or (vi) heteroaryl substituted with zero to 6 $R^c$;

$R^3$ is:
  (i) H, halo, —CN, —$OR^d$, —$NR^eR^e$, or —$C(O)OR^f$;
  (ii) $C_{1-6}$alkyl substituted with zero to 4 $R^a$; or
  (iii) $C_{3-6}$ cycloalkyl substituted with zero to 4 $R^a$;

or $R^2$ and $R^3$ can be combined to form:
  (i) a 5- to 6-membered aryl fused radical substituted with zero to 2 $R^a$; or
  (ii) a 5- to 6-membered heteroaryl fused radical comprising one heteroatom, wherein said heteroaryl fused radical is substituted with zero to 2 $R^a$;

each $R^a$ is independently halo, —OH, —CN, $C_{3-6}$cycloalkyl, $C_{1-2}$fluoroalkyl, $C_{1-6}$alkoxy, $C_{1-2}$fluoroalkoxy, —$NR^fR^f$, phenyl substituted with zero to 5 $R^b$, phenoxy substituted with zero to 4 $R^b$, heterocyclyl substituted with zero to 4 $R^c$, and/or heteroaryl substituted with zero to 4 $R^b$;

each $R^b$ is independently halo, —OH, —CN, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, —C(O)OH, —$S(O)_2(C_{1-4}$alkyl), —$S(O)_2 NR^fR^f$, and/or heterocyclyl substituted with zero to 4 $R^c$;

each $R^c$ is independently halo, —CN, —OH, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, azetidine, and/or pyrrolidine, or two $R^c$ attached to the same atom can form =O;

each $R^d$ is:
  (i) $C_{1-4}$alkyl substituted with zero to 4 $R^a$;
  (ii) $C_{3-6}$ cycloalkyl substituted with zero to 4 $R^a$;
  (iii) aryl substituted with zero to 6 $R^b$;
  (iv) heterocyclyl substituted with zero to 6 $R^c$; and/or
  (v) heteroaryl substituted with zero to 6 $R^c$;

each $R^e$ is independently:
  (i) H;
  (ii) $C_{1-4}$alkyl substituted with zero to 4 $R^a$; and/or
  (iii) $C_{3-6}$ cycloalkyl substituted with zero to 4 $R^a$;

or two $R^e$ attached to the same nitrogen atom can form a 5-6 membered heterocyclyl ring having one additional heteroatom, and substituted with zero to 2 substituents independently selected from —CN, —OH, and/or $C_{1-4}$alkyl:

and each $R^f$ is independently H, $C_{1-6}$alkyl, $C_{3-6}$cycloalkyl, $C_{1-4}$fluoroalkyl, and/or aryl.

One embodiment provides compounds of Formula (I), pharmaceutically acceptable salts or prodrugs thereof, wherein Z is CH. The compounds of this embodiment have the structure of Formula (II):

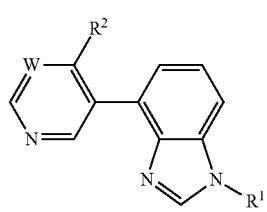

(II)

wherein W, $R^1$, and $R^2$ are defined in the first aspect of the invention hereinabove.

One embodiment provides compounds of Formula (I), pharmaceutically acceptable salts or prodrugs thereof, wherein Z is N. The compounds of this embodiment have the structure of Formula (III):

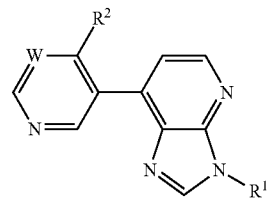

(III)

wherein W, $R^1$, and $R^2$ are defined in the first aspect of the invention hereinabove.

One embodiment provides compounds of Formula (I), pharmaceutically acceptable salts or prodrugs thereof, wherein W is $CR^3$. The compounds of this embodiment have the structure of Formula (IV):

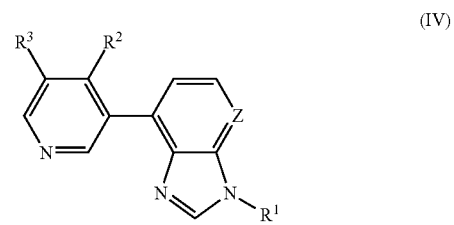

(IV)

wherein X, $R^1$, $R^2$, and $R^3$ are defined in the first aspect of the invention hereinabove.

One embodiment provides compounds of Formula (I), pharmaceutically acceptable salts or prodrugs thereof, wherein W is N. The compounds of this embodiment have the structure of Formula (V):

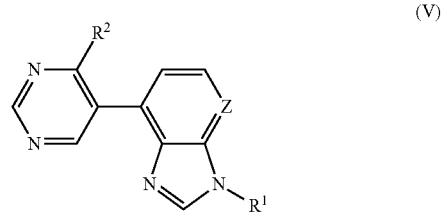

(V)

wherein X, $R^1$, and $R^2$ are defined in the first aspect of the invention hereinabove.

One embodiment provides compounds of Formula (I), pharmaceutically acceptable salts or prodrugs thereof, wherein W is N and Z is CH. The compounds of this embodiment have the structure of Formula (VI):

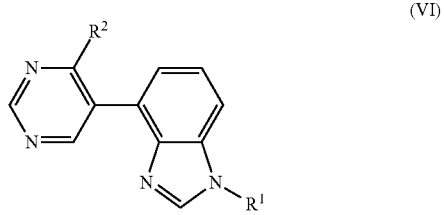

(VI)

wherein $R^1$ and $R^2$ are defined in the first aspect of the invention hereinabove.

One embodiment provides compounds of Formula (I), pharmaceutically acceptable salts or prodrugs thereof, wherein W is N and Z is N. The compounds of this embodiment have the structure of Formula (VII):

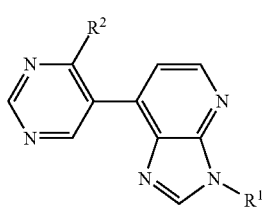

(VII)

wherein $R^1$ and $R^2$ are defined in the first aspect of the invention hereinabove.

One embodiment provides compounds of Formula (I), pharmaceutically acceptable salts or prodrugs thereof, wherein W is $CR^3$ and Z is CH. The compounds of this embodiment have the structure of Formula (VIII):

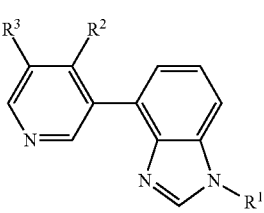

(VIII)

wherein $R^1$, $R^2$, and $R^3$ are defined in the first aspect of the invention hereinabove.

One embodiment provides compounds of Formula (I), pharmaceutically acceptable salts or prodrugs thereof, wherein W is $CR^3$ and Z is N. The compounds of this embodiment have the structure of Formula (IX):

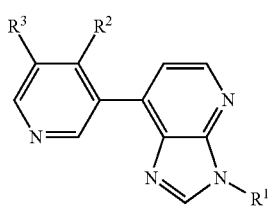

(IX)

wherein $R^1$, $R^2$, and $R^3$ are defined in the first aspect of the invention hereinabove.

One embodiment provides compounds of Formula (I), pharmaceutically acceptable salts or prodrugs thereof, wherein $R^1$ is: (i) $C_{1-4}$alkyl substituted with zero to 4 $R^a$; (ii) $C_{3-6}$ cycloalkyl substituted with zero to 2 $R^a$; (iii) —S(O)$_2$ ($C_{1-3}$alkyl), —S(O)$_2$($C_{1-2}$fluoroalkyl), or —C(O)($C_{1-4}$alkyl); (iv) phenyl or naphthalenyl substituted with zero to 4 $R^b$; or (v) 1- or 2-ring heteroaryl comprising at least nitrogen heteroatom, substituted with zero to 4 $R^c$. Included in this embodiment are compounds in which $R^1$ is: (i) $C_{1-4}$alkyl substituted with zero to 3 $R^a$; (ii) $C_{3-6}$ cycloalkyl; (iii) —S(O)$_2$ ($C_{1-3}$alkyl), —S(O)$_2$($C_{1-2}$fluoroalkyl), or —C(O) ($C_{1-4}$alkyl); (iv) phenyl substituted with zero to 4 $R^b$; or (v) thiazolyl, pyridinyl, pyridazinyl, pyrimidinyl, pyrazinyl, benzothiazolyl, or isoquinolinyl substituted with zero to 3 $R^c$. Also included in this embodiment are compounds in which $R^1$ is: (i) —CH$_2$CN, or —CH$_2$CH$_2$F, —CH$_2$CF$_3$, or —CH$_2$(phenyl); (ii) cyclopropyl; (iii) —S(O)$_2$(CH$_2$CH$_3$) or —C(O) CH(CH$_3$)$_2$; or (iv) phenyl, thiazolyl, pyridinyl, pyridazinyl, pyrimidinyl, or pyrazinyl substituted with zero to 2 substituents independently selected from F, Cl, —CN, —CH$_3$, —CF$_3$, and/or —OCH$_3$; or (iv) benzothiazolyl or isoquinolinyl.

One embodiment provides compounds of Formula (I), pharmaceutically acceptable salts or prodrugs thereof, wherein $R^2$ is: (i) H, F, Cl, —OR$^d$, —NHR$^e$, or —C(O)O($C_{1-4}$ alkyl); (ii) $C_{1-4}$alkyl substituted with zero to 4 $R^a$; or (iii) $C_{3-6}$ cycloalkyl. Included in this embodiment are compounds in which $R^2$ is: (i) H, $C_1$, $C_{1-2}$alkoxy, —NHR$^e$, or —C(O)OCH$_3$; or (ii) —CH$_3$, —CF$_3$, —CH$_2$OH, —CHCl$_2$, or —CH$_2$CN. Also included in this embodiment are compounds in which $R^2$ is Cl, —CH$_3$, —CH$_2$OH, $C_{1-2}$alkoxy, or —NH$_2$.

One embodiment provides compounds of Formula (I), pharmaceutically acceptable salts or prodrugs thereof, wherein $R^3$ is: (i) H, F, Cl, —CN, —OR$^d$, —NHR$^e$, —C(O) O($C_{1-4}$alkyl); or (ii) $C_{1-4}$alkyl substituted with zero to 4 $R^a$. Included in this embodiment are compounds in which $R^3$ is H.

One embodiment provides compounds of Formula (I), pharmaceutically acceptable salts or prodrugs thereof, wherein $R^2$ and $R^3$ are combined to form: (i) a 5- to 6-membered aryl fused radical substituted with zero to 1 $R^a$; or (ii) a 5- to 6-membered heteroaryl fused radical comprising one heteroatom, wherein said heteroaryl fused radical is substituted with zero to 1 $R^a$. Included in this embodiment are compounds in which $R^2$ and $R^3$ are combined to form a 5- to 6-membered aryl fused radical substituted with zero to 1 $R^a$, having the structures:

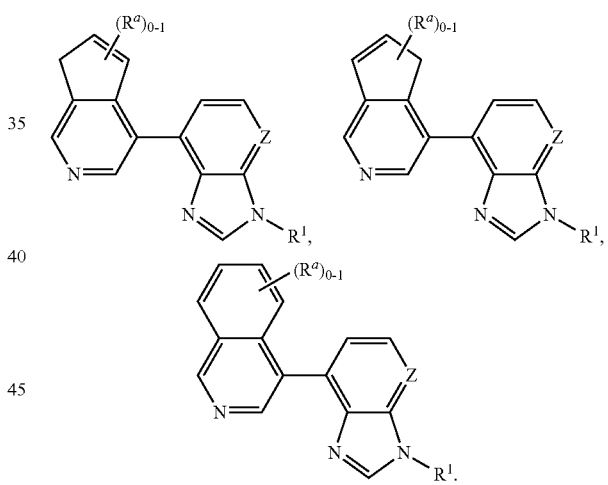

Also included in this embodiment are compounds in which $R^2$ and $R^3$ are combined to form a 5- to 6-membered heteroaryl fused radical substituted with zero to 1 $R^a$. Examples of such compounds include:

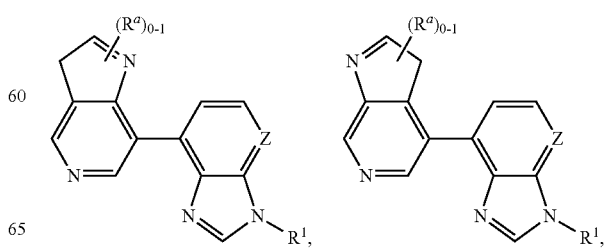

-continued

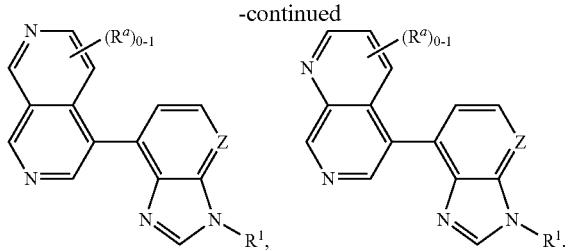

One embodiment provides compounds of Formula (I), pharmaceutically acceptable salts or prodrugs thereof, wherein each $R^a$ is independently F, Cl, —OH, —CN, $C_{3-6}$cycloalkyl, $C_{1-2}$fluoroalkyl, $C_{1-2}$fluoroalkoxy, and/or phenyl substituted with zero to 4 $R^b$. Included in this embodiment are compounds in which each $R^a$ is independently F, —OH, —CN, —CF$_3$, and/or phenyl substituted with zero to 2 $R^b$.

One embodiment provides compounds of Formula (I), pharmaceutically acceptable salts or prodrugs thereof, wherein each $R^b$ is independently F, Cl, Br, —OH, —CN, $C_{1-4}$alkyl, $C_{3-6}$cycloalkyl, $C_{1-2}$fluoroalkyl, $C_{1-2}$alkoxy, $C_{1-2}$fluoroalkoxy, —NH$_2$, —NH(CH$_3$), —N(CH$_3$)$_2$, —C(O)OH, —S(O)$_2$(C$_{1-4}$alkyl), and/or —S(O)$_2$NR$^f$R$^f$. Included in this embodiment are compounds in which each $R^b$ is independently F, Cl, Br, —CN, C$_{1-3}$alkyl, —CF$_3$, C$_{1-2}$alkoxy, —OCF$_3$, —C(O)OH, and/or —S(O)$_2$NH$_2$.

One embodiment provides compounds of Formula (I), pharmaceutically acceptable salts or prodrugs thereof, wherein each $R^c$ is independently F, Cl, Br, —CN, —OH, C$_{1-4}$alkyl, C$_{3-6}$cycloalkyl, C$_{1-2}$fluoroalkyl, C$_{1-2}$alkoxy, C$_{1-2}$fluoroalkoxy, —NH$_2$, —NH(CH$_3$), and/or —N(CH$_3$)$_2$. Included in this embodiment are compounds in which each $R^c$ is independently F, Cl, Br, —CN, —OH, C$_{1-3}$alkyl, —CF$_3$, and/or C$_{1-2}$alkoxy.

One embodiment provides compounds of Formula (I), pharmaceutically acceptable salts or prodrugs thereof, wherein $R^d$ is C$_{1-4}$alkyl substituted with zero to 4 $R^a$.

One embodiment provides compounds of Formula (I), pharmaceutically acceptable salts or prodrugs thereof, wherein each $R^e$ is independently H and/or C$_{1-4}$alkyl substituted with zero to 4 $R^a$. Included in this embodiment are compounds in which $R^e$ is H or C$_{1-2}$fluoroalkyl.

One embodiment provides compounds of Formula (I), pharmaceutically acceptable salts or prodrugs thereof, wherein:
Z is CH or N;
W is CR$^3$ or N;
$R^1$ is:
  (i) C$_{1-4}$alkyl substituted with zero to 4 R$^a$;
  (ii) C$_{3-6}$ cycloalkyl substituted with zero to 2 R$^a$;
  (iii) —S(O)$_2$(C$_{1-3}$alkyl), —S(O)$_2$(C$_{1-2}$ fluoroalkyl), or —C(O)(C$_{1-4}$alkyl);
  (iv) phenyl or naphthalenyl substituted with zero to 4 R$^b$; or
  (v) 1- or 2-ring heteroaryl comprising at least nitrogen heteroatom, substituted with zero to 4 R$^c$;
$R^2$ is:
  (i) H, F, Cl, —OR$^d$, —NHR$^e$, or —C(O)O(C$_{1-4}$alkyl);
  (ii) C$_{1-4}$alkyl substituted with zero to 4 R$^a$; or
  (iii) C$_{3-6}$ cycloalkyl;
$R^3$ is:
  (i) H, F, Cl, —CN, —OR$^d$, —NHR$^e$, —C(O)O(C$_{1-4}$alkyl); or
  (ii) C$_{1-4}$alkyl substituted with zero to 4 R$^a$;
or R$^2$ and R$^3$ can be combined to form:
  (i) a 5- to 6-membered aryl fused radical substituted with zero to 1 R$^a$; or
  (ii) a 5- to 6-membered heteroaryl fused radical comprising one heteroatom, wherein said heteroaryl fused radical is substituted with zero to 1 R$^a$;
each R$^a$ is independently F, Cl, —OH, —CN, C$_{3-6}$cycloalkyl, C$_{1-2}$fluoroalkyl, C$_{1-2}$fluoroalkoxy, and/or phenyl substituted with zero to 4 R$^b$;
each R$^b$ is independently F, Cl, Br, —OH, —CN, C$_{1-4}$alkyl, C$_{3-6}$cycloalkyl, C$_{1-2}$fluoroalkyl, C$_{1-2}$alkoxy, C$_{1-2}$fluoroalkoxy, —NH$_2$, —NH(CH$_3$), —N(CH$_3$)$_2$, —C(O)OH, —S(O)$_2$(C$_{1-4}$alkyl), and/or —S(O)$_2$NR$^f$R$^f$;
each R$^c$ is independently F, Cl, Br, —CN, —OH, C$_{1-4}$alkyl, C$_{3-6}$cycloalkyl, C$_{1-2}$fluoroalkyl, C$_{1-2}$alkoxy, C$_{1-2}$fluoroalkoxy, —NH$_2$, —NH(CH$_3$), and/or —N(CH$_3$)$_2$;
R$^d$ is C$_{1-4}$alkyl substituted with zero to 4 R$^a$; and
each R$^e$ is independently H and/or C$_{1-4}$alkyl substituted with zero to 4 R$^a$.

One embodiment provides compounds of Formula (I), pharmaceutically acceptable salts or prodrugs thereof, wherein:
Z is CH or N;
W is CR$^3$ or N;
$R^1$ is:
  (i) C$_{1-4}$alkyl substituted with zero to 3 R$^a$;
  (ii) C$_{3-6}$ cycloalkyl;
  (iii) —S(O)$_2$(C$_{1-3}$alkyl), —S(O)$_2$(C$_{1-2}$fluoroalkyl), or —C(O)(C$_{1-4}$alkyl);
  (iv) phenyl substituted with zero to 4 R$^b$; or
  (v) thiazolyl, pyridinyl, pyridazinyl, pyrimidinyl, pyrazinyl, benzothiazolyl, or isoquinolinyl substituted with zero to 3 R$^c$;
$R^2$ is:
  (i) H, C$_1$, C$_{1-2}$alkoxy, —NHR$^e$, or —C(O)OCH$_3$; or
  (ii) —CH$_3$, —CF$_3$, —CH$_2$OH, —CHCl$_2$, or —CH$_2$CN;
$R^3$ is H;
or R$^2$ and R$^3$ can be combined to form 6-membered aryl fused radical;
each R$^a$ is independently F, —OH, —CN, —CF$_3$, and/or phenyl substituted with zero to 2 R$^b$;
each R$^b$ is independently F, Cl, Br, —CN, C$_{1-3}$ alkyl, —CF$_3$, C$_{1-2}$alkoxy, —OCF$_3$, —C(O)OH, and/or —S(O)$_2$NH$_2$;
each R$^c$ is independently F, Cl, Br, —CN, —OH, C$_{1-3}$ alkyl, —CF$_3$, and/or C$_{1-2}$alkoxy; and
R$^e$ is H or C$_{1-2}$fluoroalkyl.

One embodiment provides compounds of Formula (I), pharmaceutically acceptable salts or prodrugs thereof, wherein:
Z is CH or N;
W is CR$^3$ or N;
$R^1$ is:
  (i) —CH$_2$CN, or —CH$_2$CH$_2$F, —CH$_2$CF$_3$, or —CH$_2$(phenyl);
  (ii) cyclopropyl;
  (iii) —S(O)$_2$(CH$_2$CH$_3$) or —C(O)CH(CH$_3$)$_2$; or
  (iv) phenyl, thiazolyl, pyridinyl, pyridazinyl, pyrimidinyl, or pyrazinyl substituted with zero to 2 substituents independently selected from F, Cl, —CN, —CH$_3$, —CF$_3$, and/or —OCH$_3$; or
  (v) benzothiazolyl or isoquinolinyl; and
R$^2$ is Cl, —CH$_3$, —CH$_2$OH, C$_{1-2}$alkoxy, or —NH$_2$;
R$^3$ is H;
or R$^2$ and R$^3$ can be combined to form 6-membered aryl fused radical.

One embodiment provides compounds of Formula (I), pharmaceutically acceptable salts or prodrugs thereof, wherein said compound is selected from 4-(4-methylpyridin- 3-yl)-1-phenyl-1H-benzo[d]imidazole (1); 4-(4-methylpyridin-3-yl)-1-(pyridin-2-yl)-1H-benzo[d]imidazole (2); 4-(4-(4-methylpyridin-3-yl)-1H-benzo[d]imidazol-1-yl)thiazole (3); 4-(4-methylpyridin-3-yl)-1-(pyrazin-2-yl)-1H-benzo[d]imidazole (4); 2-(4-(4-methylpyridin-3-yl)-1H-benzo[d]imidazol-1-yl)thiazole (5); 4-(4-methylpyridin-3-yl)-1-(pyridazin-3-yl)-1H-benzo[d]imidazole (6); 2-(4-(4-methylpyridin-3-yl)-1H-benzo[d]imidazol-1-yl)benzonitrile (7); 4-(4-methylpyridin-3-yl)-1-(pyrimidin-5-yl)-1H-benzo[d]imidazole (8); 4-(4-methylpyridin-3-yl)-1-(6-(trifluoromethyl)pyridin-2-yl)-1H-benzo[d]imidazole (9); 4-(4-methylpyridin-3-yl)-1-(4-(trifluoromethyl)pyridin-2-yl)-1H-benzo[d]imidazole (10); 4-(4-methylpyridin-3-yl)-1-(3-(trifluoromethyl)pyridin-2-yl)-1H-benzo[d]imidazole (11); 1-(3-methoxypyridin-2-yl)-4-(4-methylpyridin-3-yl)-1H-benzo[d]imidazole (12); 1-(5-fluoropyridin-2-yl)-4-(4-methylpyridin-3-yl)-1H-benzo[d]imidazole (13); 1-(6-fluoropyridin-2-yl)-4-(4-methylpyridin-3-yl)-1H-benzo[d]imidazole (14); 1-(3,5-difluoropyridin-2-yl)-4-(4-methylpyridin-3-yl)-1H-benzo[d]imidazole (15); 1-(4-fluorophenyl)-4-(4-methylpyridin-3-yl)-1H-benzo[d]imidazole (16); 4-(4-methylpyridin-3-yl)-1-(pyridin-3-yl)-1H-benzo[d]imidazole (17); 1-(6-chloropyridin-2-yl)-4-(4-methylpyridin-3-yl)-1H-benzo[d]imidazole (18); 2-(4-(4-methylpyridin-3-yl)-1H-benzo[d]imidazol-1-yl)nicotinonitrile (19); 2-(4-(4-methylpyridin-3-yl)-1H-benzo[d]imidazol-1-yl)quinoline (20); 2-(4-(4-methylpyridin-3-yl)-1H-benzo[d]imidazol-1-yl)benzo[d]thiazole (21); 1-(2-methoxypyridin-3-yl)-4-(4-methylpyridin-3-yl)-1H-benzo[d]imidazole (22); 1-(3-chloropyridin-2-yl)-4-(4-methylpyridin-3-yl)-1H-benzo[d]imidazole (23); 1-(5-fluoropyridin-3-yl)-4-(4-methylpyridin-3-yl)-1H-benzo[d]imidazole (24); 1-(3-fluoropyridin-2-yl)-4-(4-methylpyridin-3-yl)-1H-benzo[d]imidazole (25); 4-methyl-2-(4-(4-methylpyridin-3-yl)-1H-benzo[d]imidazol-1-yl)thiazole (26); 4-(4-methylpyridin-3-yl)-1-(4-(trifluoromethyl)pyridin-3-yl)-1H-benzo[d]imidazole (27); 5-methyl-2-(4-(4-methylpyridin-3-yl)-1H-benzo[d]imidazol-1-yl)thiazole (28); 4-(4-methylpyridin-3-yl)-1-(pyrimidin-4-yl)-1H-benzo[d]imidazole (29); 4-(4-methylpyridin-3-yl)-1-(pyridin-4-yl)-1H-benzo[d]imidazole (30); 4-(4-methylpyridin-3-yl)-1-(2,2,2-trifluoroethyl)-1H-benzo[d]imidazole (31); 1-benzyl-4-(4-methylpyridin-3-yl)-1H-benzo[d]imidazole (32); 1-(ethylsulfonyl)-4-(4-methylpyridin-3-yl)-1H-benzo[d]imidazole (33); 2-methyl-1-(4-(4-methylpyridin-3-yl)-1H-benzo[d]imidazol-1-yl)propan-1-one (34); 2-(4-(4-methylpyridin-3-yl)-1H-benzo[d]imidazol-1-yl)acetonitrile (35); 1-(2-fluoroethyl)-4-(4-methylpyridin-3-yl)-1H-benzo[d]imidazole (36); 1-cyclopropyl-4-(4-methylpyridin-3-yl)-1H-benzo[d]imidazole (37); (3-(1-(2,2,2-trifluoroethyl)-1H-benzo[d]imidazol-4-yl)pyridin-4-yl)methanol (38); 4-(4-chloropyridin-3-yl)-1-(2,2,2-trifluoroethyl)-1H-benzo[d]imidazole (39); 4-(4-chloropyridin-3-yl)-1-(ethylsulfonyl)-1H-benzo[d]imidazole (40); 4-(4-methoxypyridin-3-yl)-1-(2,2,2-trifluoroethyl)-1H-benzo[d]imidazole (41); 1-(ethylsulfonyl)-4-(4-methoxypyridin-3-yl)-1H-benzo[d]imidazole (42); 4-(4-methylpyrimidin-5-yl)-1-(pyridin-2-yl)-1H-benzo[d]imidazole (43); 5-(1-(2,2,2-trifluoroethyl)-1H-benzo[d]imidazol-4-yl)pyrimidin-4-amine (44); 4-(4-ethoxypyrimidin-5-yl)-1-(2,2,2-trifluoroethyl)-1H-benzo[d]imidazole (45); 5-(1-(2,4-difluorophenyl)-1H-benzo[d]imidazol-4-yl)pyrimidin-4-amine (46); 5-(1-(4-fluorophenyl)-1H-benzo[d]imidazol-4-yl)pyrimidin-4-amine (47); 4-(1-(6-fluoropyridin-2-yl)-1H-benzo[d]imidazol-4-yl)isoquinoline (48); 4-(1-(pyridin-2-yl)-1H-benzo[d]imidazol-4-yl)isoquinoline (49); and 7-(4-methylpyridin-3-yl)-3-(2,2,2-trifluoroethyl)-3H-imidazo[4,5-b]pyridine (50).

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—CH$_2$Cl), trifluoromethyl (—CF$_3$—, and 2,2,2-trifluoroethyl (—CH$_2$CF$_3$). When numbers appear in a subscript after the symbol "C", the subscript defines with more specificity the number of carbon atoms that a particular haloalkyl group may contain. For example, "C$_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "cyano" refers to the group —CN.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_3$-C$_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$).

"Fluoroalkoxy" and "—O(fluoroalkyl)" represent a fluoroalkyl group as defined above attached through an oxygen linkage (—O—). For example, "C$_{1-4}$fluoroalkoxy" is intended to include C$_1$, C$_2$, C$_3$, and C$_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,*

17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)]salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes amides and carbamates formed by reacting one or more amino groups of compounds of Formula (I) with alkyl, alkoxy, or aryl substituted acylating agents employing procedures known to those skilled in the art to generate amides, ureas, carbamates, and the like.

Various forms of prodrugs are well known in the art and are described in:
a) Wermuth, C. G. et al., *The Practice of Medicinal Chemistry*, Ch. 31, Academic Press (1996);
b) Bundgaard, H., ed., *Design of Prodrugs*, Elsevier (1985);
c) Krogsgaard-Larson, P. et al., eds., *A Textbook of Drug Design and Development*, Ch. 5, pp. 113-191, Harwood Academic Publishers (1991); and
d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of CYP17 enzyme, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.05 and about 50 mg/kg body weight and most preferably between about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

UTILITY

The compounds of Formula (I) are useful for the treatment of cancer, for example, cancers dependent upon androgen receptor signaling. These compounds inhibit the activity of the CYP17 enzyme, which is involved in biosynthesis of androgens and estrogens. Blocking this enzyme would inhibit the production of gonadal, adrenal, and tumoral androgens and offers a new treatment option for cancers dependent upon androgen receptor and estrogen receptor signaling, such as prostate cancer and estrogen receptor-positive breast cancer patients. Thus, the treatment comprises administering to the patient a compound of Formula (I) or a pharmaceutically acceptable salt or prodrug thereof.

In one embodiment, a method is provided for treating cancer comprising administering compound of Formula (I) or a pharmaceutically acceptable salt or prodrug thereof to a mammal in need thereof. The method of this embodiment can be used to treat a variety of cancers, including, but not limited to, breast cancer, ovarian cancer, and prostate cancer. Preferably, the method of this embodiment is used to treat prostate cancer or breast cancer. In one method of this embodiment, compound of Formula (I) is administered in a therapeutically effective amount.

In one embodiment, provided are methods for treating cancer in a patient wherein the cancer is dependent upon CYP17 activation, comprising administering to the patient in need thereof a compound of Formula (I) or a pharmaceutically acceptable salt or prodrug thereof. In one method of this embodiment, a compound of Formula (I) is administered to treat prostate cancer. In another method of this embodiment, a compound of Formula (I) is administered to treat breast cancer. Preferably, a therapeutically effective amount of Compound (1) is administered.

In one embodiment, a method is provided for treating benign prostatic hyperplasia comprising administering compound of Formula (I) or a pharmaceutically acceptable salt or prodrug thereof to a mammal in need thereof. In this embodiment, the compound of Formula (I) can be administered as a single agent or in combination with one or more other agents for the treatment of benign prostatic hyperplasia. In one method of this embodiment, compound of Formula (I) is administered in a therapeutically effective amount.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.05 and about 50 mg/kg body weight and most preferably between about 0.05 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the *Physicians' Desk Reference* (PDR) or as otherwise determined by one of ordinary skill in the art.

In one embodiment, a method is provided for treating cancer comprising administering to a mammal in need thereof a compound of Formula (I) or a pharmaceutically acceptable salt or prodrug thereof; administering a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I) or a pharmaceutically acceptable salt or prodrug thereof; administering a mineralocorticoid receptor antagonist; and optionally, one or more additional anticancer agent. Examples of suitable mineralocorticoid receptor antagonists include, but are not limited to, eplerenone.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

In one embodiment, the use of a compound of Formula (I) or a pharmaceutically acceptable salt thereof in the manufacture of a medicament for the treatment of cancer, including breast cancer, is provided.

METHODS OF PREPARATION

The compounds of the present invention may be prepared by synthetic routes that include processes analogous to those well-known in the chemical arts, particularly in light of the description provided herein. For illustrative purposes, general Schemes 1-13 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art.

As shown in Scheme 1, for instance, N1-aryl substituted benzimidazoles of type I can be prepared from an aryl boronic acid or ester of general structure II and a benzimidazole halide of type III. Under standard Suzuki coupling conditions, a product of general structure IV is formed. A subsequent reaction of this intermediate with an aryl or heteroaryl halide under palladium catalysis provides the N1-aryl substituted benzimidazole of type I.

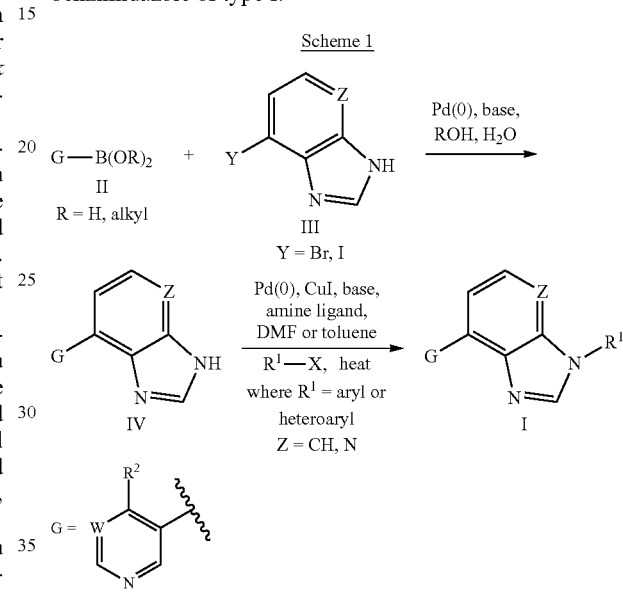

Scheme 1

The general structure of the aryl boronic acid or ester of type II shown in Scheme 1 can be synthesized from the corresponding halide V by a palladium-mediated reaction with a source of boron or alternatively through halogen-metal exchange and a subsequent reaction with triisopropyl borate (Scheme 2).

Scheme 2

$$G-Y \xrightarrow[\substack{\text{or}\\ \text{n-BuLi, B(OR)}_3\text{, THF, -78° C.}\\ \text{or}\\ \text{Pd(II), ligand, base, HB(OR)}_2,\\ \text{dioxane, heat}}]{\substack{(RO)_2B-B(OR)_2\\ \text{Pd(II), KOAc, DMSO, heat}}} G-B(OR)_2$$

V, Y = Br, I   →   II

The general halides of type V used in the synthesis of aryl boronic acid or ester II can originate from pyrimidyl ethers VII (Scheme 3), pyrimidyl amines VIII (Scheme 4), 4-alkyl or 4-aryl pyrimidines X (Scheme 5), 4-aryl pyridines XII (Scheme 6), and 4-cycloalkyl XIV or 4-alkyl pyridines XIV, XV (Scheme 7 and 8). Each of these halides can be synthesized in the following manner. The pyrimidyl ethers VII can be generated from displacement of the corresponding pyrimidyl chloride VI with an alcohol and base. The pyrimidyl amines VIII can be synthesized under the same reaction conditions from the pyrimidyl chloride VI and ammonia or a primary or secondary amine 4-Alkyl and 4-aryl substituted pyrimidines can be prepared by many methods well known to those skilled in the art. Scheme 5 depicts one such method where 5-bromopyrimidine can be treated with an alkyl or aryl lithium or a Grignard reagent to give the 4-substituted dihydropyrimidine. Subsequent oxidation by, for example, DDQ, then gives the desired 4-substituted pyrimidine X. In contrast, 4-aryl pyridines of general structure XII can be prepared by Suzuki coupling of boronic ester XI with an aryl iodide under palladium catalysis. Finally, substituted pyridines of type XIV and XV can be synthesized by deprotonation of 3-bromopyridine with a strong base such as LDA to generate an anion, and then a subsequent reaction with an alkyl or cycloalkyl ketone to give substituted pyridines of type XIV or treatment with an alkyl iodide to afford 4-alkyl pyridines of type XV.

Scheme 3

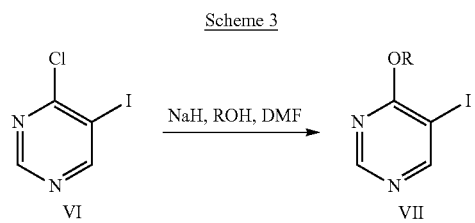

Scheme 4

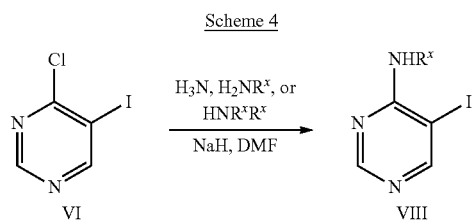

R$^x$ = alkyl, aryl, or cycloalkyl

Scheme 5

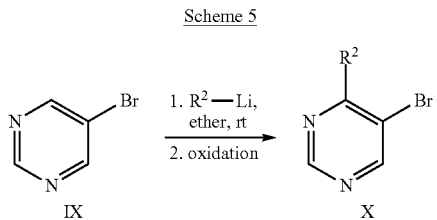

R$^2$ = alkyl or aryl

Scheme 6

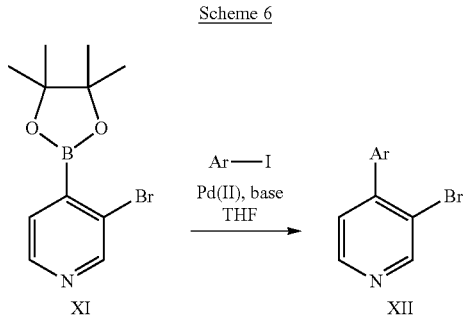

Scheme 7

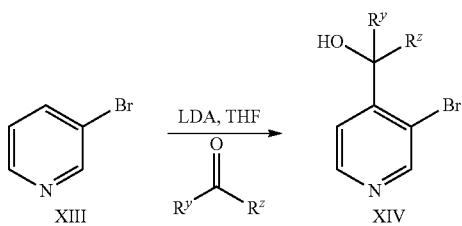

Scheme 8

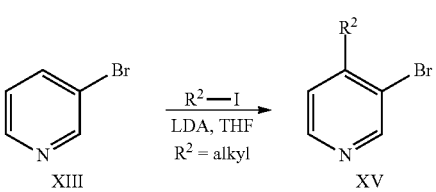

Alternatively, N1-aryl substituted benzimidazoles of type I can be prepared from a copper-based coupling of benzimidazole intermediate III with an aryl or heteroaryl boronic acid to yield N1-aryl benzimidazole XVI (Scheme 9). Under standard Suzuki coupling conditions, reaction of this intermediate with an aryl boronic acid or ester of general structure II also furnishes N1-aryl substituted benzimidazoles of type I.

Scheme 9

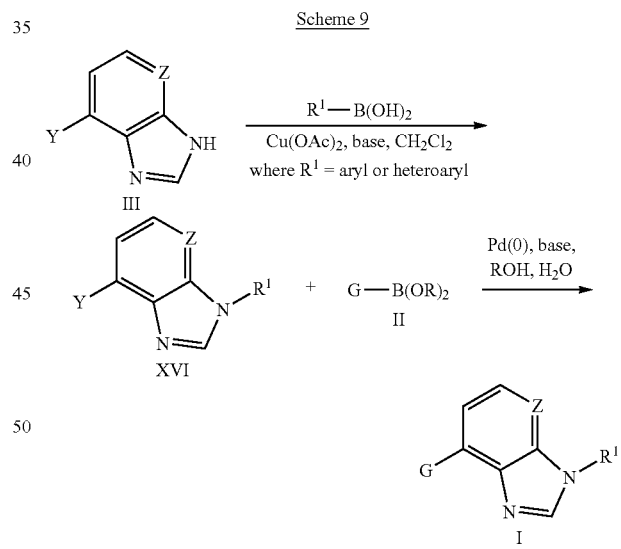

Y = Br, I
R = H, alkyl

The intermediate of general structure IV can also be utilized in the synthesis of N1-alkyl, acyl, and sulfonyl benzimidazoles (Scheme 10). Treatment of benzimidazole IV with an alkyl halide in the presence of base and a solvent, such as DMF or DMSO, yields compounds of type I with alkyl substitution at N1. Alternatively, replacement of the alkyl halide with an acyl chloride or a sulfonyl halide under the same reaction conditions would afford N1-acyl benzimidazoles or N1-sulfonyl benzimidazoles, also of general structure I.

Scheme 10

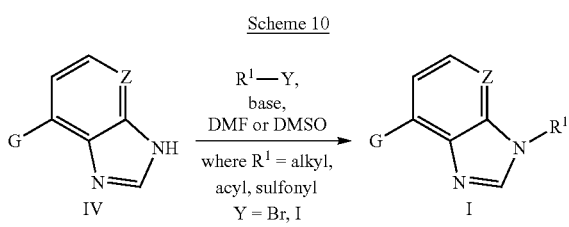

The method of preparing substituted benzimidazoles linked to hydroxyl methyl pyridines of type XX is depicted in Scheme 11. Starting with a 4-methylpyridyl-linked benzimidazole of general structure XVII, reaction with an oxidant such as m-CPBA, furnishes N-oxide XVIII. Acetylation of the N-oxide moiety with acetic anhydride leads to Boekelheide rearrangement product XIX. Saponification of the acetate with a base such as potassium carbonate and methanol gives the corresponding hydroxyl methyl pyridine of general structure XX.

Scheme 11

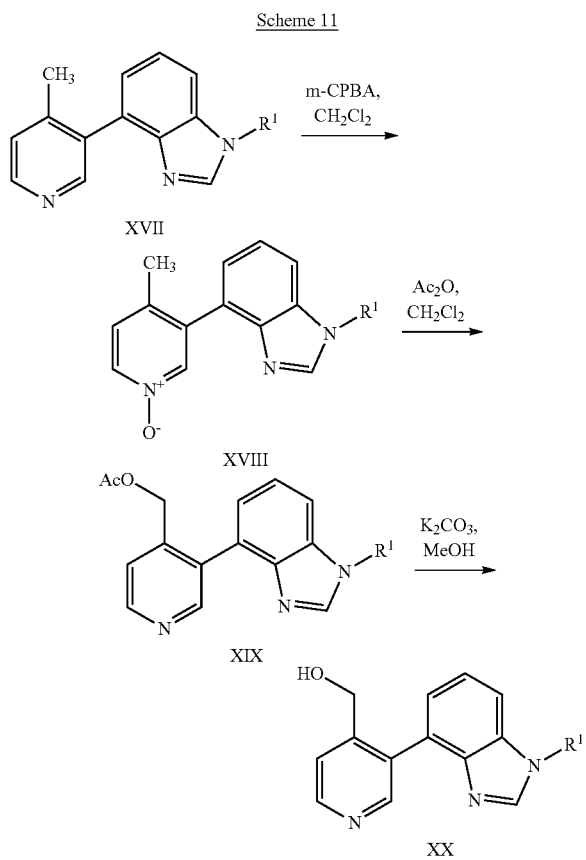

As shown in Scheme 12, benzimidazoles linked to substituted pyrimidines of general structure XXV can be synthesized from intermediate XXI by the following sequence. Reaction of benzimidazole XXI with an alkyl halide, sulfonyl halide or an acyl chloride in the presence of base and a solvent, such as DMF or DMSO, leads to the corresponding N1-substituted product XXII. Treatment of this compound with peracetic acid and sulfuric acid in acetone furnishes 4-hydroxyl pyrimidine XXIII. Subsequently, the hydroxyl group can be reacted with phosphorus oxychloride to provide 4-chloro pyrimidine XXIV. Finally, displacement of the chlorine can be accomplished by treatment with an amine or alcohol source in the presence of base to yield amines or ethers at the 4-position of the pyrimidine of the general structure XXV.

Scheme 12

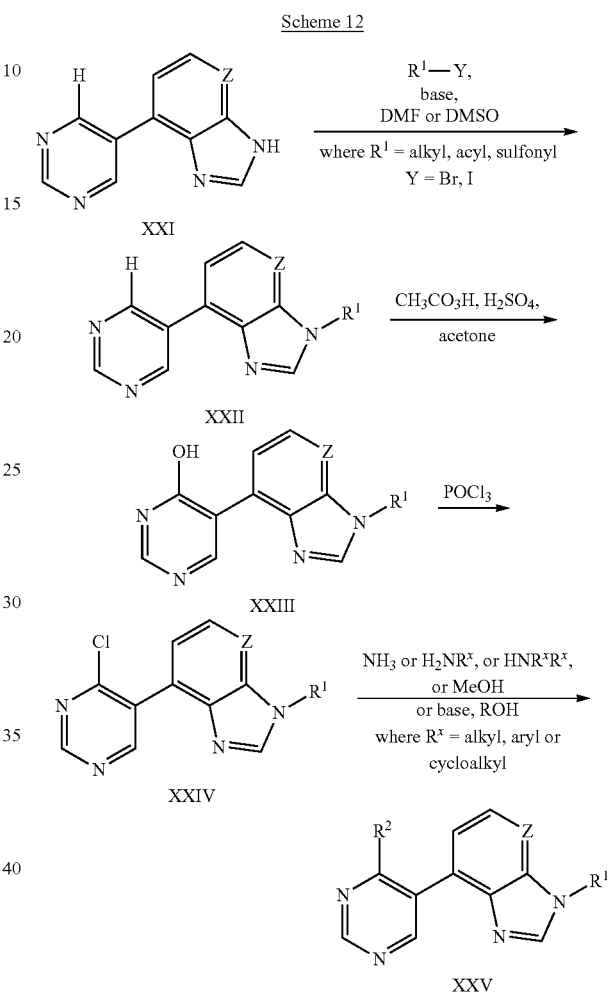

Scheme 13 depicts the synthesis of N1-alkyl, acyl, and sulfonyl imidazopyridines of type XXVI. Starting from commercially available imidazopyridine XXVII, displacement of the chloride with a nucleophilic source of iodide such as HI yields the imidazopyridine iodide of general structure XXVIII. Reaction of imidazopyridine XXVIII with an alkyl halide, sulfonyl halide or an acyl chloride in the presence of base and a solvent, such as DMF or DMSO, leads to the corresponding N1-substituted product of general structure XXVI.

Scheme 13

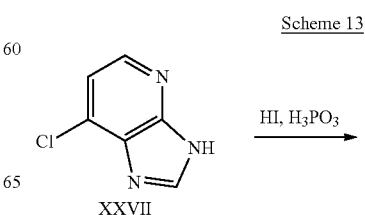

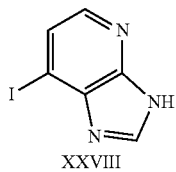

XXVIII

-continued

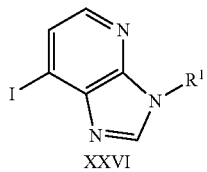

where R¹ = alkyl, acyl, sulfonyl
Y = Br, I

XXVI

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm)

ABBREVIATIONS

ACN acetonitrile
aq. aqueous
$CH_2Cl_2$ dichloromethane
DCE 1,2-dichloroethane
DDQ 2,3-dichloro-5,6-dicyano-p-benzoquinone
DME dimethyl ether
DMF dimethylformamide
DMSO dimethylsulfoxide
Et ethyl
EtOAc ethyl acetate
EtOH ethanol
g gram(s)
h hour
HCl hydrochloric acid
HPLC high performance liquid chromatography
$H_2SO_4$ sulfuric acid
KOAc potassium acetate
LC/MS liquid chromatography/mass spectrometry
LDA lithium diisopropylamide
m-CPBA 3-chloroperbenzoic acid
Me methyl
MeOH methanol
mg milligram(s).
min minute
mL milliliter
mmol millimole(s).
μmol micromole(s).
MS mass spectrometry
n-BuLi n-butyl lithium
$NH_3$ ammonia
$NH_4OAc$ ammonium acetate
ret. T or $t_r$ HPLC retention time (minutes).
RT or rt room temperature
sat or sat'd saturated
TFA trifluoroacetic acid
THF tetrahydrofuran Example 1

4-(4-Methylpyridin-3-yl)-1-phenyl-1H-benzo[d]imidazole

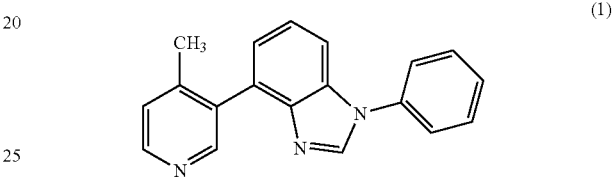

(1)

Preparation 1A:
4-(4-Methylpyridin-3-yl)-1H-benzo[d]imidazole

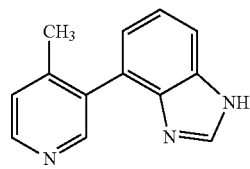

(1A)

A vial was charged with tetrakis(triphenylphosphine)palladium(0) (0.129 g, 0.112 mmol), 4-bromo-1H-benzo[d]imidazole (0.200 g, 1.015 mmol), sodium carbonate (0.430 g, 4.06 mmol), and 4-methylpyridin-3-ylboronic acid (0.146 g, 1.066 mmol). The mixture was stirred at room temperature for 10 min under $N_2$, then water (1.894 mL), DME (3.79 mL), and EtOH (1.894 mL) were added sequentially. The resultant mixture was stirred under $N_2$ for 15 min, then heated at 90° C. overnight. After 21.5 h, the reaction mixture was allowed to cool to room temperature, then quenched with water and diluted with EtOAc. The layers were separated and the aqueous phase extracted with EtOAc (3×). The organic phases were combined, dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (40 g column, 40 mL/min, 1-20% MeOH in $CH_2Cl_2$ over 30 min, $t_r$=20 min) gave the title compound (132 mg, 0.631 mmol, 62.1% yield) as a white foam. ESI MS (M+H)⁺=210.0. HPLC Peak $t_r$=14.20 minutes. Purity >99%. HPLC conditions: Xbridge Phenyl column, 4.6×150 mm. 30 min gradient (10-100% B), 2 mL/min, 23° C. @ 220 nm, Solvent A: 10 mM $NH_4HCO_3$ pH 9.5 in $H_2O$:MeOH (95:5), Solvent B: 10 mM $NH_4HCO_3$ pH 9.5 in $H_2O$:MeOH (5:95).

Example 1

A vial was charged with Preparation 1A (25 mg, 0.119 mmol), copper(I) iodide (1.138 mg, 5.97 μmol), and cesium carbonate (82 mg, 0.251 mmol). The reaction vessel was fitted with a rubber septum, evacuated, and back-filled with $N_2$. This evacuation/back-fill sequence was repeated one additional time. To this mixture were added iodobenzene (16.04 μL, 0.143 mmol), (1R,2R)—N1,N2-dimethylcyclohexane-1,2-diamine (3.77 μL, 0.024 mmol), and DMF (119 μL) under $N_2$. The reaction vial was quickly sealed and the contents were stirred while heating in a metal pie block at 110° C. After 24 h, the reaction mixture was allowed to cool to room temperature. Upon cooling to room temperature, the heterogeneous mixture was filtered through a disposable fritted funnel and the filter cake washed with $CH_2Cl_2$ (10 mL). The filtrate was concentrated and the crude material was chromatographed by silica gel chromatography using an ISCO machine (12 g column, 30 mL/min, 0-20% MeOH in $CH_2Cl_2$ over 35 min) to afford the title compound (17.5 mg, 0.060 mmol, 50.3% yield) ($t_r$=14 min) as a colorless solid and the starting pyridyl benzimidazole (8.0 mg, 32%) ($t_r$=24 min) as a colorless film. ESI MS $(M+H)^+$=286.1. HPLC Peak $t_r$=1.882 minutes. Purity=98%. HPLC conditions: YMC S5 ODS column, 4.6×50 mm. 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

TABLE 1

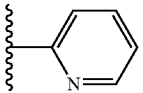

| Ex. | R | Compound Name | Mol Wt | [M + H] | Ret time |
|---|---|---|---|---|---|
| 2 | 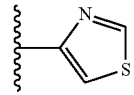 | 4-(4-methylpyridin-3-yl)-1-(pyridin-2-yl)-1H-benzo[d]imidazole | 286.33 | 287.1 | 1.65[a] |
| 3 | 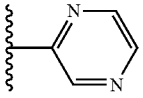 | 4-(4-(4-methylpyridin-3-yl)-1H-benzo[d]imidazol-1-yl)thiazole | 292.36 | 293.0 | 1.88[b] |
| 4 | 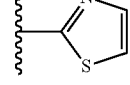 | 4-(4-methylpyridin-3-yl)-1-(pyrazin-2-yl)-1H-benzo[d]imidazole | 287.32 | 288.1 | 1.45[a] |
| 5 | 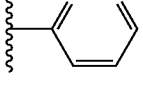 | 2-(4-(4-methylpyridin-3-yl)-1H-benzo[d]imidazol-1-yl)thiazole | 292.36 | 293.1 | 1.63[a] |
| 6 | 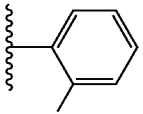 | 4-(4-methylpyridin-3-yl)-1-(pyridazin-3-yl)-1H-benzo[d]imidazole | 287.32 | 288.1 | 1.20[a] |
| 7 | 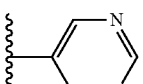 | 2-(4-(4-methylpyridin-3-yl)-1H-benzo[d]imidazol-1-yl)benzonitrile | 310.35 | 311.1 | 1.89[b] |
| 8 | 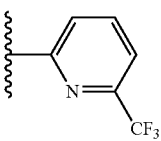 | 4-(4-methylpyridin-3-yl)-1-(pyrimidin-5-yl)-1H-benzo[d]imidazole | 287.32 | 288.1 | 1.07[a] |
| 9 |  | 4-(4-methylpyridin-3-yl)-1-(6-(trifluoromethyl)pyridin-2-yl)-1H-benzo[d]imidazole | 354.33 | 355.1 | 2.48[a] |

TABLE 1-continued

[Structure: 4-methylpyridin-3-yl connected to benzo[d]imidazole with N-R substituent]

| Ex. | R | Compound Name | Mol Wt | [M + H] | Ret time |
|---|---|---|---|---|---|
| 10 | 4-(trifluoromethyl)pyridin-2-yl (CF$_3$ at 4-position) | 4-(4-methylpyridin-3-yl)-1-(4-(trifluoromethyl)pyridin-2-yl)-1H-benzo[d]imidazole | 354.33 | 355.1 | 2.43$^b$ |
| 11 | 3-(trifluoromethyl)pyridin-2-yl (F$_3$C at 3-position) | 4-(4-methylpyridin-3-yl)-1-(3-(trifluoromethyl)pyridin-2-yl)-1H-benzo[d]imidazole | 354.33 | 355.1 | 2.03$^b$ |
| 12 | 3-methoxypyridin-2-yl (H$_3$CO) | 1-(3-methoxypyridin-2-yl)-4-(4-methylpyridin-3-yl)-1H-benzo[d]imidazole | 316.36 | 317.1 | 1.99$^b$ |
| 13 | 5-fluoropyridin-2-yl | 1-(5-fluoropyridin-2-yl)-4-(4-methylpyridin-3-yl)-1H-benzo[d]imidazole | 304.32 | 305.1 | 2.00$^b$ |
| 14 | 6-fluoropyridin-2-yl | 1-(6-fluoropyridin-2-yl)-4-(4-methylpyridin-3-yl)-1H-benzo[d]imidazole | 304.32 | 305.1 | 2.09$^b$ |
| 15 | 3,5-difluoropyridin-2-yl | 1-(3,5-difluoropyridin-2-yl)-4-(4-methylpyridin-3-yl)-1H-benzo[d]imidazole | 322.31 | 323.2 | 1.91$^b$ |
| 16 | 4-fluorophenyl (shown as 5-F pyridine) | 1-(4-fluorophenyl)-4-(4-methylpyridin-3-yl)-1H-benzo[d]imidazole | 303.33 | 304.2 | 2.15$^b$ |

Condition A: HPLC conditions: YMC S5 ODS column, 4.6 x 50 mm. 4 min gradient (0-100% B), 4 mL/min, 40° C. @ 220 nm; Solvent A: 0.2% H$_3$PO$_4$ in 10% MeOH – 90% H$_2$O, Solvent B: 0.2% H$_3$PO$_4$ in 90% MeOH – 10% H$_2$O.
Condition B: Column: Mac-mod Halo C18, 4.6 x 50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

The following compounds were synthesized from Preparation 1A and the respective halide using the following procedure: To a 16×100 mm Wheaton tube was added Preparation 1A (1.0 eq, 0.1 mmol) followed with dioxane (500 µL). To this solution was then added an aryl halide (2.0 eq, 0.2 mmol), copper iodide (0.1 eq, 0.01 mmol), (1R,2R)-(−)-1,2-diaminocyclohexane (0.6 eq, 0.06 mmol), and potassium phosphate (2.1 eq, 0.2 µmol). The tube was capped, air evacuated and vial was purged with N$_2$. The reaction mixture was agitated at 400 rpm on an INNOVA® platform shaker at 120° C. overnight. Samples were then placed in the SPEEDVAC® to dry for 2 hours at 45° C. The solid material was dissolved in 1.5 mL of DMF and submitted at such for purification. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient adjusted accordingly to isolate product; Flow: 20 mL/min. Fractions containing the desired product were combined and dried via centrifugal evaporation. All compounds were analyzed using the following HPLC conditions: Column: SUPELCO® Ascentis Express C18, 4.6×50 mm, 2.7-µm particles; Mobile Phase A: 10:90 acetonitrile:water with 0.1% TFA; Mobile Phase B: 90:10 acetonitrile:water with 0.1% TFA; Temperature: 23° C.; Gradient: 0-100% B over 4 minutes, then a 1-minute hold at 100% B; Flow: 4 mL/min.

TABLE 2

| Ex. | R | Name | Mol Wt | [M + H] | Ret time |
|---|---|---|---|---|---|
| 17 | pyridin-3-yl | 4-(4-methylpyridin-3-yl)-1-(pyridin-3-yl)-1H-benzo[d]imidazole | 286.33 | 287.22 | 1.51 |
| 18 | 6-chloropyridin-2-yl | 1-(6-chloropyridin-2-yl)-4-(4-methylpyridin-3-yl)-1H-benzo[d]imidazole | 320.78 | 321.16 | 2.27 |
| 19 | 3-cyanopyridin-2-yl | 2-(4-(4-methylpyridin-3-yl)-1H-benzo[d]imidazol-1-yl)nicotinonitrile | 311.34 | 312.15 | 1.71 |
| 20 | quinolin-2-yl | 2-(4-(4-methylpyridin-3-yl)-1H-benzo[d]imidazol-1-yl)quinoline | 336.39 | 337.19 | 2.49 |
| 21 | benzo[d]thiazol-2-yl | 2-(4-(4-methylpyridin-3-yl)-1H-benzo[d]imidazol-1-yl)benzo[d]thiazole | 342.42 | 343.14 | 2.63 |
| 22 | 2-methoxypyridin-3-yl | 1-(2-methoxypyridin-3-yl)-4-(4-methylpyridin-3-yl)-1H-benzo[d]imidazole | 316.36 | 317.19 | 1.91 |
| 23 | 3-chloropyridin-2-yl | 1-(3-chloropyridin-2-yl)-4-(4-methylpyridin-3-yl)-1H-benzo[d]imidazole | 320.78 | 321.16 | 1.9 |
| 24 | 5-fluoropyridin-3-yl | 1-(5-fluoropyridin-3-yl)-4-(4-methylpyridin-3-yl)-1H-benzo[d]imidazole | 304.32 | 305.11 | 1.72 |
| 25 | 3-fluoropyridin-2-yl | 1-(3-fluoropyridin-2-yl)-4-(4-methylpyridin-3-yl)-1H-benzo[d]imidazole | 304.32 | 305.17 | 1.87 |
| 26 | 4-methylthiazol-2-yl | 4-methyl-2-(4-(4-methylpyridin-3-yl)-1H-benzo[d]imidazol-1-yl)thiazole | 306.39 | 307.19 | 2.14 |

TABLE 2-continued

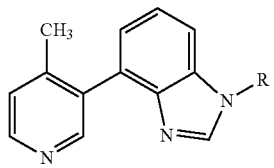

| Ex. | R | Name | Mol Wt | [M + H] | Ret time |
|---|---|---|---|---|---|
| 27 | | 4-(4-methylpyridin-3-yl)-1-(4-(trifluoromethyl)pyridin-3-yl)-1H-benzo[d]imidazole | 354.33 | 355.15 | 1.87 |
| 28 | | 5-methyl-2-(4-(4-methylpyridin-3-yl)-1H-benzo[d]imidazol-1-yl)thiazole | 306.39 | 307.2 | 2.14 |
| 29 | | 4-(4-methylpyridin-3-yl)-1-(pyrimidin-4-yl)-1H-benzo[d]imidazole | 287.32 | 288.14 | 1.62 |
| 30 | | 4-(4-methylpyridin-3-yl)-1-(pyridin-4-yl)-1H-benzo[d]imidazole | 286.33 | 287.22 | 1.52 |

Example 31

4-(4-Methylpyridin-3-yl)-1-(2,2,2-trifluoroethyl)-1H-benzo[d]imidazole

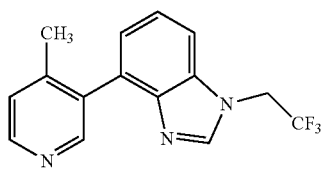

(31)

To a solution of Preparation 1A (0.230 g, 1.10 mmol) in DMSO (7.69 mL) was added cesium carbonate (0.716 g, 2.198 mmol) and 2,2,2-trifluoroethyl trifluoromethanesulfonate (0.268 g, 1.154 mmol). After 4 h, the reaction was quenched with $H_2O$ and diluted with EtOAc. The layers were separated and the aqueous phase was extracted with EtOAc (3×). The combined organic phases were washed with $H_2O$ (2×) and brine (1×), then dried over $Na_2SO_4$, filtered, and concentrated to afford a yellow residue. The crude material was dissolved in a minimal amount of $CH_2Cl_2$ and chromatographed. Purification of the crude material by silica gel chromatography using an ISCO machine (40 g column, 40 mL/min, 1-10% MeOH in $CH_2Cl_2$ over 30 min, $t_r$=23 min) gave the title compound (216 mg, 0.742 mmol, 67.5% yield) as a white solid. $^1H$ NMR (500 MHz, MeOD) δ ppm 8.44 (1H, d, J=5.3 Hz), 8.42 (1H, s), 8.27 (1H, s), 7.75 (1H, d, J=8.3 Hz), 7.48-7.54 (1H, m), 7.42 (1H, d, J=5.0 Hz), 7.22-7.28 (1H, m), 5.24 (2H, q, J=8.9 Hz), 2.22 (3H, s); $^{13}C$ NMR (126 MHz, MeOD) δ ppm 150.50, 148.99, 148.97, 146.07, 142.32, 136.51, 135.56, 130.49, 126.84, 125.27, 125.25, 125.36 (q, J=277.9 Hz, 1C), 111.82, 46.63 (q, J=35.4 Hz, 1C), 20.14; ESI MS $(M+H)^+$=292.2. HPLC Peak $t_r$=1.438 minutes. Purity >99%. HPLC conditions: YMC S5 ODS column, 4.6× 50 mm. 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

Example 32

1-Benzyl-4-(4-methylpyridin-3-yl)-1H-benzo[d]imidazole

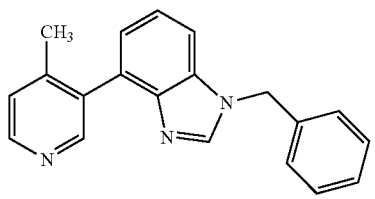

(32)

To a solution of Preparation 1A (25 mg, 0.119 mmol) in DMSO (835 μL) was added cesium carbonate (78 mg, 0.239 mmol) and (bromomethyl)benzene (14.92 μL, 0.125 mmol). After 4 h, the reaction was quenched with a saturated aqueous solution of $NH_4Cl$ and diluted with EtOAc. The layers were separated and the aqueous phase extracted with EtOAc (3×). The organic layers were combined, dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (12 g column, 30 mL/min, 0-20% MeOH in $CH_2Cl_2$ over 30 min, $t_r$=15 min)

gave the title compound (21.7 mg, 0.070 mmol, 58.8% yield) as a colorless film. ESI MS (M+H)+=300.2. HPLC Peak $t_r$=1.537 minutes. Purity=97%. HPLC conditions: YMC S5 ODS column, 4.6×50 mm. 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

Example 33

1-(Ethylsulfonyl)-4-(4-methylpyridin-3-yl)-1H-benzo[d]imidazole

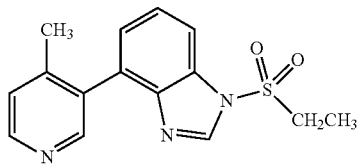

(33)

To a solution of Preparation 1A (25 mg, 0.119 mmol) in DMSO (835 µL) was added cesium carbonate (78 mg, 0.239 mmol) and ethanesulfonyl chloride (11.89 µL, 0.125 mmol). After 24 h, the reaction was quenched with a saturated aqueous solution of $NH_4Cl$ and diluted with EtOAc. The layers were separated and the aqueous phase extracted with EtOAc (3×). The organic layers were combined, dried over $Na_2SO_4$, filtered, and concentrated to afford a yellow residue. The crude material was dissolved in a minimal amount of $CH_2Cl_2$ and chromatographed. Purification of the crude material by silica gel chromatography using an ISCO machine (12 g column, 30 mL/min, 0-20% MeOH in $CH_2Cl_2$ over 30 min, $t_r$=9 min) gave the title compound (10.8 mg, 0.036 mmol, 30.0% yield) as a colorless film. ESI MS (M+H)+=302.0. HPLC Peak $t_r$=1.385 minutes. Purity >99%. HPLC conditions: YMC S5 ODS column, 4.6×50 mm. 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

Example 34

2-Methyl-1-(4-(4-methylpyridin-3-yl)-1H-benzo[d]imidazol-1-yl)propan-1-one

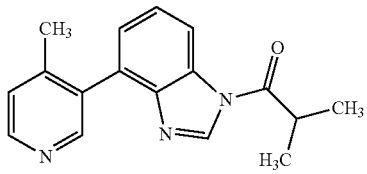

(34)

To a solution of Preparation 1A (25 mg, 0.119 mmol) and cesium carbonate (78 mg, 0.239 mmol) in DMF (835 µL) was added isobutyryl chloride (13.77 µL, 0.131 mmol). After 24 h, the reaction was quenched with a saturated aqueous solution of $NH_4Cl$ and diluted with EtOAc. The layers were separated and the aqueous phase extracted with EtOAc (3×). The organic layers were combined, dried over $Na_2SO_4$, filtered, and concentrated to afford a yellow residue. The crude material was dissolved in a minimal amount of $CH_2Cl_2$ and chromatographed. Purification of the crude material by silica gel chromatography using an ISCO machine (12 g column, 30 mL/min, 0-20% MeOH in $CH_2Cl_2$ over 30 min, $t_r$=9 min) gave the title compound (18.4 mg, 0.065 mmol, 54.0% yield) as a colorless film. ESI MS (M+H)+=280.1. HPLC Peak $t_r$=1.892 minutes. Purity=98%. HPLC conditions: YMC S5 ODS column, 4.6×50 mm. 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

Example 35

2-(4-(4-Methylpyridin-3-yl)-1H-benzo[d]imidazol-1-yl)acetonitrile

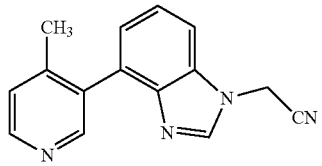

(35)

To a solution of Preparation 1A (0.0205 g, 0.098 mmol) in DMSO (0.685 mL) was added cesium carbonate (0.064 g, 0.196 mmol) and 2-bromoacetonitrile (6.82 µL, 0.098 mmol). The reaction mixture was stirred at room temperature for 20 h, then quenched with $H_2O$ and extracted with EtOAc (6×). Organics combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 0.05% TFA; Mobile Phase B: 95:5 methanol:water with 0.05% TFA; Gradient: 0-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-45% B over 25 minutes, then a 15-minute hold at 45% B; Flow: 20 mL/min. Fractions containing the desired product were combined and dried via centrifugal evaporation to afford the title compound (7.2 mg, 30%). ESI MS (M+H)+=249.1. HPLC Peak $t_r$=1.527 minutes. Purity >99%. HPLC conditions: Mac-mod Halo C18, 4.6×50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 36

1-(2-Fluoroethyl)-4-(4-methylpyridin-3-yl)-1H-benzo[d]imidazole

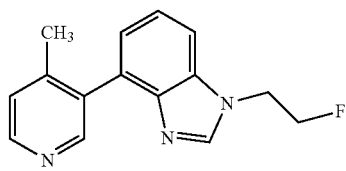

(36)

To a solution of Preparation 1A (0.021 g, 0.100 mmol) in DMSO (0.702 mL) was added cesium carbonate (0.065 g, 0.201 mmol) and 1-bromo-2-fluoroethane (9.16 µL, 0.120 mmol). The reaction mixture was stirred at room temperature for 15 h, then quenched with $H_2O$ and extracted with EtOAc (6×). Organics combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 15-85% B over 25 minutes, then a 5-minute hold at 85% B; Flow: 20 mL/min. Fractions containing the desired product were combined and dried via centrifugal evaporation to afford the title compound (18 mg, 68%). ESI MS $(M+H)^+$=256.2. HPLC Peak $t_r$=1.512 minutes. Purity >99%. HPLC conditions: Mac-mod Halo C18, 4.6×50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 37

1-Cyclopropyl-4-(4-methylpyridin-3-yl)-1H-benzo[d]imidazole

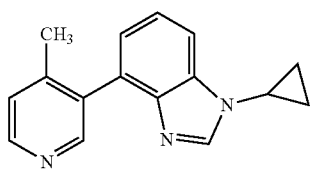

(37)

A suspension of cyclopropylboronic acid (20.94 mg, 0.244 mmol), Preparation 1A (25.5 mg, 0.122 mmol), sodium carbonate (25.8 mg, 0.244 mmol), copper (II) acetate (22.13 mg, 0.122 mmol), and 2,2'-bipyridine (19.03 mg, 0.122 mmol) in DCE (1219 µL) was heated at 70° C. for 17 h. The resulting mixture was cooled to room temperature, filtered through a disposable fritted funnel, then treated with a solution of saturated aqueous $NH_4Cl$ and diluted with $CH_2Cl_2$. The layers were separated and the aqueous phase extracted with $CH_2Cl_2$ (2×). The organic layers were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (2.1 mg, 6.9%). ESI MS $(M+H)^+$=250.2. HPLC Peak $t_r$=1.750 minutes. Purity >99%. HPLC conditions: Mac-mod Halo C18, 4.6×50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 38

(3-(1-(2,2,2-Trifluoroethyl)-1H-benzo[d]imidazol-4-yl)pyridin-4-yl)methanol

(38)

Preparation 38A: 4-Methyl-3-(1-(2,2,2-trifluoroethyl)-1H-benzo[d]imidazol-4-yl)pyridine 1-oxide

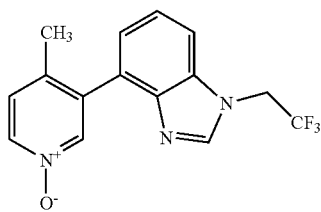

(38A)

To a solution of Example 31 (0.065 g, 0.223 mmol) in $CH_2Cl_2$ (1.449 mL) was added m-CPBA (0.046 g, 0.268 mmol). After 6.5 h, the reaction was quenched with a saturated aqueous solution of $Na_2S_2O_3$ and diluted with $CH_2Cl_2$. Layers were separated and the organic phase further washed with a saturated aqueous solution of $NaHCO_3$ (1×) and brine (1×). The organic layer was dried over $Na_2SO_4$, filtered, and concentrated to afford Preparation 38A (57 mg, 82%) as an off-white foam. ESI MS $(M+H)^+$=308.2. HPLC Peak $t_r$=1.922 minutes. Purity=99%. HPLC conditions: YMC S5 ODS column, 4.6×50 mm. 4 min gradient (0-100% B), 4

Preparation 38B: (3-(1-(2,2,2-Trifluoroethyl)-1H-benzo[d]imidazol-4-yl)pyridin-4-yl)methyl acetate

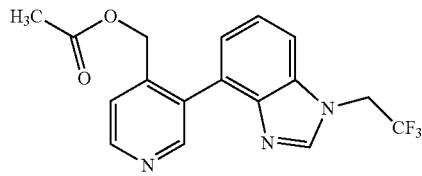
(38B)

A solution of Preparation 38A (7.4 mg, 0.024 mmol) in acetic anhydride (100 µl, 1.058 mmol) was stirred at room temperature overnight. A cloudy yellow suspension formed. The reaction became homogenous overnight and turned orange. After 10 h, only partial conversion to the desired product was attained. The reaction mixture was heated at 110° C. for 4.5 h, then allowed to cool to room temperature. The reaction mixture was concentrated to remove acetic anhydride and further dried under high vacuum. The crude material was dissolved in a minimal amount of $CH_2Cl_2$ and chromatographed. Purification of the crude material by silica gel chromatography using an ISCO machine (4 g column, 18 mL/min, 1-10% MeOH in $CH_2Cl_2$ over 15 min, $t_r$=8 min 1st 2 spots co-eluted, $t_r$=11.5 min 3rd spot eluted) afforded Preparation 38B (3.1 mg, 8.87 µmol, 36.9% yield) as an orange residue. MS (ESI): m/z=350.2 [M+H]$^+$. HPLC Peak $t_r$=1.14 minutes. HPLC conditions: Column:Luna C18 4.6× 30 mm 3u A:10:90 $H_2O$:ACN $NH_4OAc$/B:10:90 $H_2O$:ACN $NH_4OAc$; 0%-95% B in 2 min; 4 mL/min flow.

Example 38

To a solution of Preparation 38B (3.1 mg, 8.87 µmol) in MeOH (100 µL) was added potassium carbonate (1.962 mg, 0.014 mmol). The reaction was allowed to stir at room temperature. After 4 h, reaction quenched with $H_2O$ and diluted with EtOAc. An emulsion formed, so brine was added. The layers were separated and the aqueous phase was extracted with EtOAc (2×). The organic phases were combined, dried over $Na_2SO_4$, filtered, and concentrated to afford an orange residue. The crude material was dissolved in a minimal amount of $CH_2Cl_2$ and chromatographed. Purification of the crude material by silica gel chromatography using a pipette column (eluent 1-3-5-6-10% MeOH in $CH_2Cl_2$) afforded the title compound (0.8 mg, 2.447 µmol, 27.6% yield) as a yellow film. ESI MS (M+H)$^+$=308.2. HPLC Peak $t_r$=1.098 minutes. Purity=94%. HPLC conditions: YMC S5 ODS column, 4.6× 50 mm 4 min gradient (0-100% B), 4 mL/min, 40° C. @ 220 nm, Solvent A: 0.2% $H_3PO_4$ in 10% MeOH-90% $H_2O$, Solvent B: 0.2% $H_3PO_4$ in 90% MeOH-10% $H_2O$.

Example 39

4-(4-Chloropyridin-3-yl)-1-(2,2,2-trifluoroethyl)-1H-benzo[d]imidazole

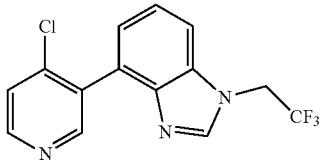
(39)

Preparation 39A: 4-(4-Chloropyridin-3-yl)-1H-benzo[d]imidazole

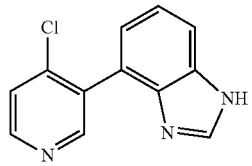
(39A)

A reaction flask was charged with tetrakis(triphenylphosphine)palladium(0) (0.022 g, 0.019 mmol), 4-bromo-1H-benzo[d]imidazole (0.075 g, 0.381 mmol), sodium carbonate (0.161 g, 1.523 mmol), and 4-chloro-3-(4,4,5,5-tetramethyl-1,3,2-dioxaborolan-2-yl)pyridine (0.137 g, 0.571 mmol). The mixture was stirred at room temperature for 10 min under $N_2$, then DME (1.420 mL), EtOH (0.710 mL), and water (0.710 mL) were added sequentially. The resultant mixture was stirred under $N_2$ for 15 min, then heated at 90° C. overnight. After 21 h, the reaction mixture was allowed to cool to room temperature, then quenched with water and diluted with EtOAc. The layers were separated and the aqueous phase was extracted with EtOAc (3×). The organic phases were combined, dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (40 g column, 40 mL/min, 1-20% MeOH in $CH_2Cl_2$ over 30 min, $t_r$=18 min) afforded Preparation 39A (5.5 mg, 0.024 mmol, 6.29% yield) as a white solid. MS (ESI): m/z=230.0 [M+H]$^+$. HPLC Peak $t_r$=0.94 minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Example 39

To a solution of Preparation 39A (5.9 mg, 0.026 mmol) in DMSO (180 µL) was added cesium carbonate (16.74 mg, 0.051 mmol) and 2,2,2-trifluoroethyl trifluoromethanesulfonate (5.96 mg, 0.026 mmol). The reaction mixture was stirred at room temperature for 3 h, then quenched with $H_2O$ and extracted with EtOAc (6×). The organic layers were combined, dried over $Na_2SO_4$, filtered, and concentrated to afford a colorless residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (4.8 mg, 60%). ESI MS (M+H)$^+$=312.0. HPLC Peak $t_r$=1.872 minutes. Purity >99%. HPLC conditions: Mac-mod Halo C18, 4.6×50 mm, 2.7-μm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 40

4-(4-Chloropyridin-3-yl)-1-(ethylsulfonyl)-1H-benzo[d]imidazole

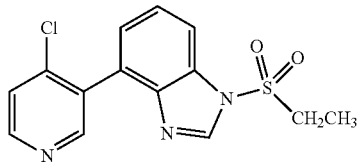

(40)

To a solution of Preparation 39A (8.7 mg, 0.038 mmol) and ethanesulfonyl chloride (4.31 μL, 0.045 mmol) in DMF (265 μL) was added sodium hydride (3.03 mg, 0.076 mmol) at room temperature. The reaction mixture was allowed to stir at room temperature overnight. After 14 h, the reaction was quenched with H$_2$O and diluted with EtOAc. The layers were separated and the aqueous phase extracted with EtOAc (3×). The combined organic phases were dried over Na$_2$SO$_4$, filtered, and concentrated to afford a colorless residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (1.9 mg, 15%). ESI MS (M+H)$^+$=322.1. HPLC Peak $t_r$=1.885 minutes. Purity=99%. HPLC conditions: Column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, then a 1-minute hold at 100% B; Flow: 4 mL/min.

Example 41

4-(4-Methoxypyridin-3-yl)-1-(2,2,2-trifluoroethyl)-1H-benzo[d]imidazole

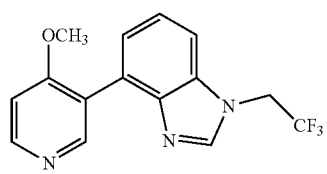

(41)

Preparation 41A:
4-(4-Methoxypyridin-3-yl)-1H-benzo[d]imidazole

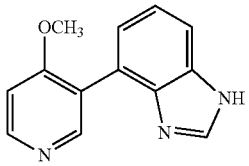

(41A)

A reaction flask was charged with tetrakis(triphenylphosphine)palladium(0) (0.024 g, 0.021 mmol), 4-bromo-1H-benzo[d]imidazole, formic acid salt (0.100 g, 0.411 mmol), sodium carbonate (0.305 g, 2.88 mmol), and 4-methoxypyridin-3-ylboronic acid, HCl (0.234 g, 1.234 mmol). The mixture was stirred at room temperature for 10 min under N$_2$, then DME (1.535 mL), EtOH (0.768 mL), and water (0.768 mL) were added sequentially. The resultant mixture was heated at 100° C. overnight. After 23 h, the reaction mixture was allowed to cool to room temperature, then quenched with water and diluted with EtOAc. The layers were separated and the aqueous phase was extracted with EtOAc (3×). The organic phases were combined, dried over Na$_2$SO$_4$, filtered, and concentrated to afford a residue. The crude material was dissolved in a minimal amount of CH$_2$Cl$_2$ and chromatographed. Purification of the crude material by silica gel chromatography using an ISCO machine (24 g column, 35 mL/min, 1-20% MeOH in CH$_2$Cl$_2$ over 30 min, $t_r$=26 min) gave Preparation 41A (16.2 mg, 0.072 mmol, 17.48% yield) as a yellow solid. MS (ESI): m/z=226.1 [M+H]$^+$. HPLC Peak $t_r$=0.89 minutes. HPLC conditions: Column:Luna C18 4.6× 30 mm 3u A:10:90 H$_2$O:ACN NH$_4$OAc/B:10:90 H$_2$O:ACN NH$_4$OAc; 0%-95% B in 2 min; 4 mL/min flow.

Example 41

To a solution of Preparation 41A (8.3 mg, 0.037 mmol) in DMSO (258 μL) was added cesium carbonate (24.01 mg, 0.074 mmol) and 2,2,2-trifluoroethyl trifluoromethanesulfonate (8.98 mg, 0.039 mmol) at room temperature. After 14 h, the reaction was quenched with H$_2$O and diluted with EtOAc. The layers were separated and the aqueous phase extracted with EtOAc (6×). The combined organic phases were dried over Na$_2$SO$_4$, filtered, and concentrated to afford a colorless residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (5.7 mg, 50%). ESI MS (M+H)⁺=308.2. HPLC Peak t,=1.645 minutes. Purity >99%. HPLC conditions: Mac-mod Halo C18, 4.6×50 mm, 2.7-μm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 42

1-(Ethylsulfonyl)-4-(4-methoxypyridin-3-yl)-1H-benzo[d]imidazole

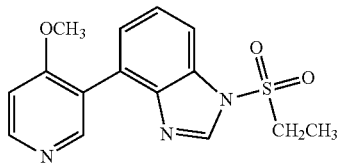

(42)

To a solution of Preparation 41A (7.9 mg, 0.035 mmol) and ethanesulfonyl chloride (3.99 μL, 0.042 mmol) in DMF (245 μL) was added sodium hydride (2.81 mg, 0.070 mmol) at room temperature. The reaction mixture was allowed to stir at room temperature overnight. After 14 h, the reaction mixture was quenched with H₂O and diluted with EtOAc. The layers were separated and the aqueous phase extracted with EtOAc (3×). The combined organic phases were dried over Na₂SO₄, filtered, and concentrated to afford a colorless residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (2.8 mg, 24%). ESI MS (M+H)⁺=318.1. HPLC Peak t,=1.625 minutes. Purity=96%. HPLC conditions: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, then a 1-minute hold at 100% B; Flow: 4 mL/min.

Example 43

4-(4-Methylpyrimidin-5-yl)-1-(pyridin-2-yl)-1H-benzo[d]imidazole

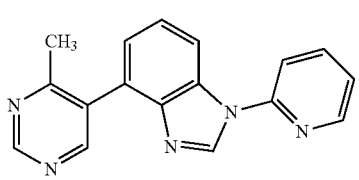

(43)

Preparation 43A: 4-Methyl-5-(4,4,5,5-tetramethyl-1,3,2-dioxaborolan-2-yl)pyrimidine

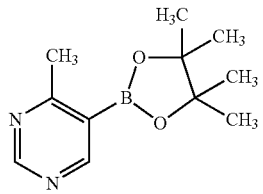

(43A)

Nitrogen was bubbled into a mixture of 5-bromo-4-methylpyrimidine (0.100 g, 0.578 mmol), 4,4,4',4',5,5,5',5'-octamethyl-2,2'-bi(1,3,2-dioxaborolane) (0.191 g, 0.751 mmol), and potassium acetate (0.129 g, 1.316 mmol) in DMSO (2.89 mL) for 10 min. Then 1,1'-bis(diphenylphosphino)ferrocenepalladium(II)dichloride dichloromethane complex (0.019 g, 0.024 mmol) was added and the reaction mixture was heated at 90° C. overnight. After 24 h, the reaction was quenched with H₂O and extracted with EtOAc (3×). The organic phases were combined, dried over Na₂SO₄, filtered, and concentrated to afford Preparation 43A as a dark brown residue. The crude material was used without further purification. MS (ESI): m/z=221.2 [M+H]⁺. HPLC Peak t,=1.11 minutes. HPLC conditions: Column:Luna C18 4.6×30 mm 3u A:10:90 H₂O:ACN NH₄OAc/B:10:90 H₂O:ACN NH₄OAc; 0%-95% B in 2 min; 4 mL/min flow.

Preparation 43B: 4-(4-Methylpyrimidin-5-yl)-1H-benzo[d]imidazole

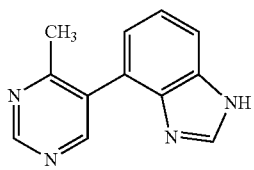

(43B)

A reaction flask was charged with tetrakis(triphenylphosphine)palladium(0) (0.012 g, 10.29 μmol), 4-bromo-1H-benzo[d]imidazole, formic acid salt (0.050 g, 0.206 mmol), sodium carbonate (0.109 g, 1.029 mmol), and Preparation 43A (0.063 g, 0.288 mmol). The mixture was stirred at room temperature for 10 min under N₂, then DME (0.768 mL), EtOH (0.384 mL), and water (0.384 mL) were added sequentially. The resultant mixture was heated at 90° C. overnight. After 19 h, the reaction mixture was allowed to cool to room temperature, then quenched with water and diluted with EtOAc. The layers were separated and the aqueous phase was extracted with EtOAc (3×). The organic phases were combined, dried over Na₂SO₄, filtered, and concentrated to afford a dark brown residue. The crude material was dissolved in a minimal amount of CH₂Cl₂ and chromatographed. Purification of the crude material by silica gel chromatography using an ISCO machine (24 g column, 35 mL/min, 1-22% MeOH in CH₂Cl₂ over 30 min, t,=24 min) gave Preparation 43B (12.0 mg, 0.057 mmol, 27.7% yield) as a red residue. MS (ESI): m/z=211.2 [M+H]⁺. HPLC Peak t,=0.73 minutes. HPLC conditions: Column:Luna C18 4.6×30 mm 3u A:10:90 H₂O:ACN NH₄OAc/B:10:90 H₂O:ACN NH₄OAc; 0%-95% B in 2 min; 4 mL/min flow.

Example 43

A vial was charged with 4-(4-methylpyrimidin-5-yl)-1H-benzo[d]imidazole (10.8 mg, 0.051 mmol), copper(I) iodide (0.489 mg, 2.57 µmol), and cesium carbonate (35.1 mg, 0.108 mmol). The reaction vessel was fitted with a rubber septum, evacuated, and back-filled with $N_2$. This evacuation/back-fill sequence was repeated one additional time. To this mixture were added 2-iodopyridine (10.92 µL, 0.103 mmol), (1R,2R)—N1,N2-dimethylcyclohexane-1,2-diamine (1.620 µL, 10.27 µmol), and DMF (51.4 µL) under $N_2$. The reaction vial was quickly sealed and the contents were stirred while heating in a metal pie block at 110° C. After 22 h, the reaction mixture was allowed to cool to room temperature. The heterogeneous mixture was filtered through a disposable fritted funnel and the filter cake washed with $CH_2Cl_2$ (10 mL). The filtrate was concentrated to afford a residue. The crude material was purified via preparative LC/MS with the following conditions: Column: Waters XBridge C18, 19×250 mm, 5-µm particles; Guard Column: Waters XBridge C18, 19×10 mm, 5-1 µm particles; Mobile Phase A: 5:95 methanol:water with 10-mM ammonium acetate; Mobile Phase B: 95:5 methanol:water with 10-mM ammonium acetate; Gradient: 40-85% B over 25 minutes, then a 10-minute hold at 85% B; Flow: 20 mL/min. Fractions containing the desired product were combined and dried via centrifugal evaporation to afford the title compound (8.3 mg, 56%). ESI MS $(M+H)^+=288.2$. HPLC Peak $t_r=2.292$ minutes. Purity >99%. HPLC conditions: Mac-mod Halo C18, 4.6×50 mm, 2.7-µm particles; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes, then a 1-minute hold at 100% B; Flow: 4 mL/min.

Example 44

5-(1-(2,2,2-Trifluoroethyl)-1H-benzo[d]imidazol-4-yl)pyrimidin-4-amine

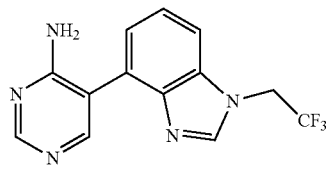

(44)

Preparation 44A:
4-(Pyrimidin-5-yl)-1H-benzo[d]imidazole

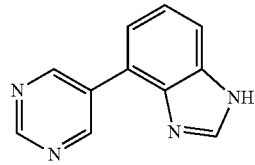

(44A)

A reaction vial was charged with tetrakis(triphenylphosphine)palladium(0) (0.024 g, 0.021 mmol), 5-(4,4,5,5-tetramethyl-1,3,2-dioxaborolan-2-yl)pyrimidine (0.148 g, 0.718 mmol), sodium carbonate (0.174 g, 1.646 mmol), and 3-(5-fluoro-2-methoxyphenyl)-7-(4,4,5,5-tetramethyl-1,3,2-dioxaborolan-2-yl)benzo[d]isoxazole (0.037 g, 0.100 mmol). The mixture was stirred at room temperature for 10 min under $N_2$, then DME (ratio: 2.0, volume: 1.535 ml), EtOH (ratio: 1.000, volume: 0.768 ml), and water (ratio: 1.000, volume: 0.768 ml) were added sequentially. The resultant mixture was heated at 90° C. overnight. After 14 h, the reaction mixture was allowed to cool to room temperature, then quenched with water and diluted with EtOAc. The layers were separated and the aqueous phase was extracted with EtOAc (3×). The organic phases were combined, dried over $Na_2SO_4$, filtered, and concentrated to afford a brown residue. The crude material was dissolved in a minimal amount of $CH_2Cl_2$ to be chromatographed. Purification of the crude material by silica gel chromatography using an ISCO machine (24 g column, 35 mL/min, 0-20% EtOAc in hexanes over 20 min, $t_r=16$ min) gave Preparation 44A (22.4 mg, 0.113 mmol, 27.5% yield) as a white solid. MS (ESI): m/z=197.1 $[M+H]^+$. HPLC Peak $t_r=1.31$ minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Preparation 44B: 4-(Pyrimidin-5-yl)-1-(2,2,2-trifluoroethyl)-1H-benzo[d]imidazole

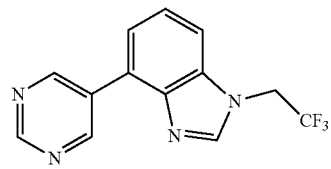

(44B)

To a solution of 4-(pyrimidin-5-yl)-1H-benzo[d]imidazole, formic acid salt (0.060 g, 0.248 mmol) in DMSO (Volume: 1.732 ml) was added cesium carbonate (0.161 g, 0.495 mmol) and 2,2,2-trifluoroethyl trifluoromethanesulfonate (0.060 g, 0.260 mmol). The reaction mixture was stirred at room temperature for 24 h, then quenched with $H_2O$ and extracted with EtOAc (5×). The organic layers were combined, dried over $Na_2SO_4$, filtered, and concentrated to afford a yellow liquid, which was further dried under high vacuum to afford a yellow solid. The crude material was dissolved in a minimal amount of $CH_2Cl_2$ and chromatographed. Purification of the crude material by silica gel chromatography using an ISCO machine (24 g column, 35 mL/min, 0-20% MeOH in $CH_2Cl_2$ over 23 min, $t_r=12$ min) gave Preparation 44B (70.7 mg, 0.252 mmol, 102% yield) as a colorless solid. MS (ESI): m/z=279.1 $[M+H]^+$. HPLC Peak $t_r=1.35$ minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Preparation 44C: 5-(1-(2,2,2-Trifluoroethyl)-1H-benzo[d]imidazol-4-yl)pyrimidin-4-ol

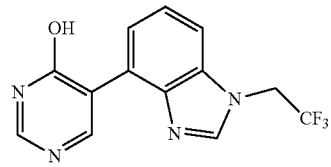

(44C)

To a vial charged with Preparation 44B (0.063 g, 0.226 mmol) in acetone (Volume: 1.348 ml) was added peroxyacetic acid (0.095 ml, 0.453 mmol) and sulfuric acid (0.025 ml, 0.453 mmol). The reaction mixture was refluxed for 1 h, then allowed to cool to room temperature. The reaction mixture was neutralized with 4 M NaOH and extracted with $CH_2Cl_2$ (8×). The organic phases were combined, dried over $Na_2SO_4$, filtered, and concentrated to afford a yellow residue. The crude material was dissolved in a minimal amount of $CH_2Cl_2$ to be chromatographed. Purification of the crude material by silica gel chromatography using an ISCO machine (12 g column, 30 mL/min, 0-30% MeOH in $CH_2Cl_2$ over 20 min, $t_r$=15 min) gave Preparation 44C (29 mg, 0.098 mmol, 43.1% yield) as a white solid. MS (ESI): m/z=295.2 $[M+H]^+$. HPLC Peak $t_r$=1.12 minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Preparation 44D: 4-(4-Chloropyrimidin-5-yl)-1-(2,2,2-trifluoroethyl)-1H-benzo[d]imidazole

(44D)

A suspension of Preparation 44C (6 mg, 0.020 mmol) in phosphorus oxychloride (101 μl, 1.081 mmol) was heated at 90° C. for 1 h, then allowed to cool to room temperature. The solvent was evaporated, and the crude material was carried forward without further purification. MS (ESI): m/z=313.1 $[M+H]^+$. HPLC Peak $t_r$=1.46 minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Example 44

A vial was charged with Preparation 44D (6.1 mg, 0.020 mmol) and freshly prepared saturated $NH_3$/MeOH (300 μL, 0.020 mmol) (bubbled ammonia gas into MeOH). The reaction mixture was sealed with a Teflon lined screw cap and heated at 130° C. After 5 min, LC-MS showed ~1.3:1 mixture of SM:product. The reaction mixture was heated at 90° C. for an additional 2 h. LC-MS showed no starting material remained. The solvent was evaporated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 5-100% B over 25 minutes, then a 5-minute hold at 100% B; Flow: 20 mL/min. Fractions containing the desired product were combined and dried via centrifugal evaporation to afford the title compound (3.0 mg, 52%). ESI MS $(M+H)^+$=294.1. HPLC Peak $t_r$=1.03 minutes. Purity=99%. HPLC conditions: Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

Example 45

4-(4-Ethoxypyrimidin-5-yl)-1-(2,2,2-trifluoroethyl)-1H-benzo[d]imidazole

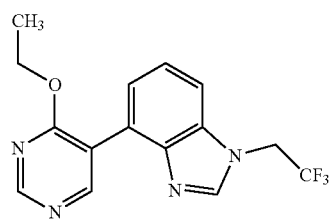

(45)

To a solution of Preparation 44D (19 mg, 0.061 mmol) and 2,2,2-trifluoroethanamine (6.32 mg, 0.064 mmol) in EtOH (Volume: 122 μl) was added Hunig's Base (23.35 μl, 0.134 mmol). The reaction mixture was refluxed for 1 h, then allowed to cool to room temperature. LC-MS showed only the product of ethoxide incorporation. The solvent was evaporated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford the title compound (9.6 mg, 49%). ESI MS $(M+H)^+$=323.1. HPLC Peak $t_r$=1.57 minutes. Purity >99%. HPLC conditions: Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

Example 46

5-(1-(2,4-Difluorophenyl)-1H-benzo[d]imidazol-4-yl)pyrimidin-4-amine

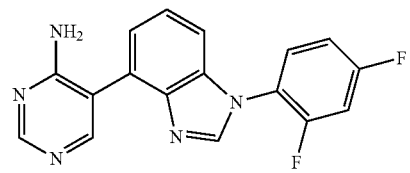

(46)

Preparation 46A: 4-Aminopyrimidin-5-ylboronic acid

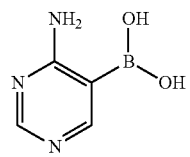
(46A)

To a vial was added 5-bromopyrimidin-4-amine (0.200 g, 1.149 mmol), bis(pinacolato)diboron (0.438 g, 1.724 mmol), and potassium acetate (0.338 g, 3.45 mmol). The vial was capped with a rubber septum and then evacuated and back-filled with $N_2$. Dioxane (volume: 0.120 ml) was added via syringe through the septum. The reaction mixture was sparged with $N_2$, then 1,1'-bis(diphenylphosphino)ferrocenedichloropalladium(II) dichloromethane complex (0.042 g, 0.057 mmol) was added. The septum was then replaced with a Teflon screw valve and the vial sealed. The reaction mixture was heated at 105° C. in a metal pie block. After 18 h, the reaction mixture was allowed to cool to room temperature. The reaction mixture was filtered through a disposable fritted funnel and the filter cake washed with EtOAc. The filtrate was concentrated to afford a brown solid. The crude material was used without further purification. MS (ESI): m/z=140.0 [M+H]$^+$. HPLC Peak $t_r$=0.24 minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Preparation 46B: 4-Bromo-1-(2,4-difluorophenyl)-1H-benzo[d]imidazole

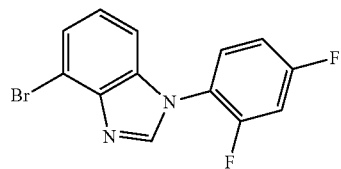
(46B)

A vial charged with molecular sieves, 4A (200 mg, 2.030 mmol) was flame-dried, then allowed to cool to room temperature. To this vial were added 4-bromo-1H-benzo[d]imidazole (0.400 g, 2.030 mmol), copper (II) acetate (0.553 g, 3.05 mmol), and 2,4-difluorophenylboronic acid (0.962 g, 6.09 mmol) followed by $CH_2Cl_2$ (Volume: 10.15 ml) and triethylamine (0.736 ml, 5.28 mmol). The heterogeneous green reaction was stirred at room temperature. After 19 h, the reaction was filtered through a disposable filter funnel and the filter cake rinsed with $CH_2Cl_2$. The filtrate was concentrated to afford a green residue. The crude material was dissolved in a minimal amount of $CH_2Cl_2$ to be chromatographed. Purification of the crude material by silica gel chromatography using an ISCO machine (12 g column, 30 mL/min, 0-45% EtOAc in hexanes over 15 min, $t_r$=10.5 min) gave Preparation 46B (7.5 mg, 0.024 mmol, 1.195% yield) as a yellow solid. MS (ESI): m/z=311.0 [M+H]$^+$. HPLC Peak $t_r$=1.73 minutes. HPLC conditions: Column:Luna C18 4.6×30 mm 3u A:10:90 $H_2O$:ACN $NH_4OAc$/B:10:90 $H_2O$:ACN $NH_4OAc$; 0%-95% B in 2 min; 4 mL/min flow.

Example 46

A vial was charged with tetrakis(triphenylphosphine)palladium(0) (1.383 mg, 1.197 mmol), Preparation 46B (7.4 mg, 0.024 mmol), sodium carbonate (10.15 mg, 0.096 mmol), and Preparation 46A (5.32 mg, 0.038 mmol). The mixture was stirred at room temperature for 10 min under $N_2$, then DME (ratio: 2.0, volume: 179 μl), EtOH (ratio: 1.000, volume: 89 μl), and water (ratio: 1.000, volume: 89 μl) were added sequentially. The resultant mixture was heated at 90° C. overnight. After 17 h, the reaction mixture was allowed to cool to room temperature, then quenched with water and diluted with EtOAc. The layers were separated and the aqueous phase was extracted with EtOAc (5×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford the title compound (2.1 mg, 27%). ESI MS (M+H)$^+$=324.1. HPLC Peak $t_r$=1.980 minutes. Purity >99%. HPLC conditions: SUPELCO® Ascentis Express C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1-minute hold at 100% B; Flow: 4 mL/min.

Example 47

5-(1-(4-Fluorophenyl)-1H-benzo[d]imidazol-4-yl)pyrimidin-4-amine

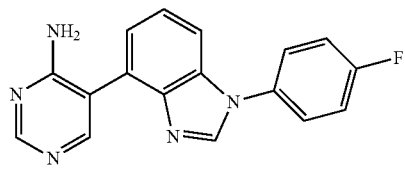
(47)

Preparation 47A: 4-Bromo-1-(4-fluorophenyl)-1H-benzo[d]imidazole

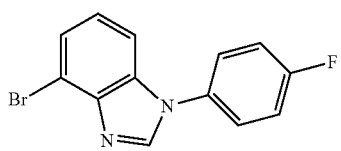
(47A)

A round bottom flask charged with molecular sieves, 4A (189 mg, 1.918 mmol) was flame-dried, then allowed to cool to room temperature. To this vial were added 4-bromo-1H-benzo[d]imidazole (0.378 g, 1.918 mmol), copper (II) acetate (0.523 g, 2.88 mmol), and 4-fluorophenylboronic acid (0.805 g, 5.76 mmol) followed by CH$_2$Cl$_2$ (Volume: 9.59 ml) and triethylamine (0.695 ml, 4.99 mmol). The heterogeneous green reaction was stirred at room temperature. After 19 h, the reaction mixture was filtered through a disposable filter funnel and the filter cake rinsed with CH$_2$Cl$_2$. The filtrate was concentrated to afford a green residue. The crude material was dissolved in a minimal amount of CH$_2$Cl$_2$ to be chromatographed. Purification of the crude material by silica gel chromatography using an ISCO machine (24 g column, 35 mL/min, 0-100% EtOAc in hexanes over 25 min, t$_r$=13 min) gave 4-bromo-1-(4-fluorophenyl)-1H-benzo[d]imidazole (158 mg, 0.299 mmol, 15.56% yield) as a white solid. LC-MS showed by-product was present. The material was re-dissolved in a minimal amount of CH$_2$Cl$_2$ (required a few drops of MeOH). Purification of the crude material by silica gel chromatography using an ISCO machine (12 g column, 30 mL/min, 0-25% EtOAc in hexanes over 13 min, t$_r$=10 min) gave Preparation 47A (158 mg, 0.299 mmol, 15.56% yield) as a white solid. LC-MS showed the product was 55% pure. The mixture was further purified by MPLC (40 g column, 36 mL/min, 30-60% EtOAc in hexanes) to afford Preparation 47A as a white solid (51 mg, 9.1%). MS (ESI): m/z=291.0 [M+H]$^+$. HPLC Peak t$_r$=1.70 minutes was product. HPLC conditions: Column:Luna C18 4.6×30 mm 3u A:10:90 H$_2$O:ACN NH$_4$OAc/B:10:90 H$_2$O:ACN NH$_4$OAc; 0%-95% B in 2 min; 4 mL/min flow.

Example 47

A vial was charged with tetrakis(triphenylphosphine)palladium(0) (5.36 mg, 4.64 µmol), Preparation 47A (27 mg, 0.093 mmol), sodium carbonate (39.3 mg, 0.371 mmol), and Preparation 46A (38.7 mg, 0.278 mmol). The mixture was stirred at room temperature for 10 min under N$_2$, then DME (Ratio: 2.0, Volume: 346 µl), EtOH (Ratio: 1.000, Volume: 173 µl), and water (Ratio: 1.000, Volume: 173 µl) were added sequentially. The resultant mixture was heated at 90° C. overnight. After 16 h, the reaction mixture was allowed to cool to room temperature, then quenched with water and diluted with EtOAc. The layers were separated and the aqueous phase was extracted with EtOAc (5×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford the title compound (2.2 mg, 7.7%). ESI MS (M+H)$^+$=306.1. HPLC Peak t$_r$=1.25 minutes. Purity >99%. HPLC conditions: Waters Acquity UPLC BEH C18, 2.1×50 mm, 1.7-µm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

Example 48

4-(1-(6-Fluoropyridin-2-yl)-1H-benzo[d]imidazol-4-yl)isoquinoline

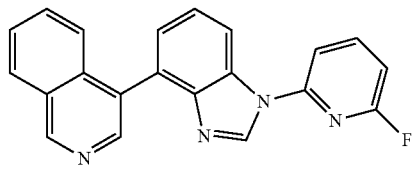

(48)

Preparation 48A:
4-(1H-Benzo[d]imidazol-4-yl)isoquinoline

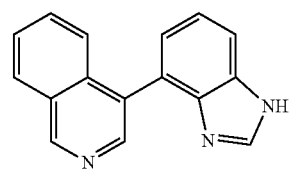

(48A)

A reaction flask was charged with tetrakis(triphenylphosphine)palladium(0) (0.036 g, 0.031 mmol), 4-bromo-1H-benzo[d]imidazole, formic acid salt (0.150 g, 0.617 mmol), sodium carbonate (0.327 g, 3.09 mmol), and 4-(4,4,5,5-tetramethyl-1,3,2-dioxaborolan-2-yl)isoquinoline (0.165 g, 0.648 mmol). The mixture was stirred at room temperature for 10 min under N$_2$, then DME (2.303 mL), EtOH (1.151 mL), and water (1.151 mL) were added sequentially. The resultant mixture was heated at 90° C. overnight. After 24 h, the reaction mixture was allowed to cool to room temperature, then quenched with water and diluted with EtOAc. The layers were separated and the aqueous phase was extracted with EtOAc (3×). The organic phases were combined, dried over Na$_2$SO$_4$, filtered, and concentrated to afford a yellow residue. The crude material was dissolved in a minimal amount of CH$_2$Cl$_2$ to be chromatographed. Purification of the crude material by silica gel chromatography using an ISCO machine (24 g column, 35 mL/min, 0-20% MeOH in CH$_2$Cl$_2$ over 25 min, t$_r$=18 min) gave Preparation 48A (0.133 g, 0.542 mmol, 88% yield) as a white foam. ESI MS (M+H)$^+$=246.2. HPLC Peak t$_r$=0.832 minutes. Purity >99%. HPLC conditions: YMC S5 ODS column, 4.6×50 mm. 4 min gradient (0-100% B), 4 mL/min, 40° C. @ 220 nm, Solvent A: 0.2% H$_3$PO$_4$ in 10% MeOH-90% H$_2$O, Solvent B: 0.2% H$_3$PO$_4$ in 90% MeOH-10% H$_2$O.

Example 48

A vial was charged with Preparation 48A (26 mg, 0.106 mmol) and cesium carbonate (72.5 mg, 0.223 mmol). To this mixture was added 2,6-difluoropyridine (24.40 mg, 0.212 mmol) in DMF (212 µL) under N$_2$. The reaction vial was quickly sealed and the contents were stirred while heating in a metal pie block at 110° C. After 14 h, the reaction mixture was allowed to cool to room temperature. The heterogeneous mixture was filtered through a disposable fritted funnel and the filter cake washed with CH$_2$Cl$_2$ (10 mL). The filtrate was concentrated to afford a residue. The crude material was purified via preparative LC/MS with the following conditions: Column: Waters XBridge C18, 19×250 mm, 5-1 µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-50% B over 30 minutes, then a 15-minute hold at 100% B; Flow: 20 mL/min. Fractions containing the desired product were combined and dried via centrifugal evaporation to afford the title compound (12 mg, 34%). ESI MS (M+H)$^+$=341.2. HPLC Peak $t_r$=2.310 minutes. Purity >99%. HPLC conditions: Column: Mac-mod Halo C18, 4.6×50 mm, 2.7-µm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, then a 1-minute hold at 100% B; Flow: 4 mL/min.

Example 49

4-(1-(Pyridin-2-yl)-1H-benzo[d]imidazol-4-yl)isoquinoline

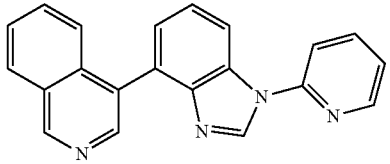

(49)

A vial was charged with Preparation 48A (26 mg, 0.106 mmol) and cesium carbonate (72.5 mg, 0.223 mmol). To this mixture was added 2-fluoropyridine (18.25 µL, 0.212 mmol) in DMF (212 µL) under N$_2$. The reaction vial was quickly sealed and the contents were stirred while heating in a metal pie block at 110° C. After 14 h, the reaction mixture was allowed to cool to room temperature. The heterogeneous mixture was filtered through a disposable fritted funnel and the filter cake washed with CH$_2$Cl$_2$ (10 mL). The filtrate was concentrated to afford a residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (20 mg, 60%). ESI MS (M+H)$^+$=323.2. HPLC Peak $t_r$=2.172 minutes. Purity >99%. HPLC conditions: Column: Mac-mod Halo C18, 4.6×50 mm, 2.7-µm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, then a 1-minute hold at 100% B; Flow: 4 mL/min.

Example 50

7-(4-Methylpyridin-3-yl)-3-(2,2,2-trifluoroethyl)-3H-imidazo[4,5-b]pyridine

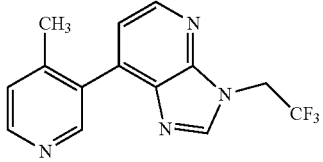

(50)

Preparation 50A: 7-Iodo-3H-imidazo[4,5-b]pyridine

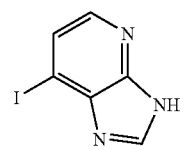

(50A)

A suspension of 7-chloro-3H-imidazo[4,5-b]pyridine (1.6 g, 10.42 mmol) and phosphorous acid (0.427 g, 5.21 mmol) in hydroiodic acid (33.3 mL, 208.4 mmol) was heated at 55° C. for 18 h and then at 70° C. for 2 h. The reaction mixture was then cooled to room temperature and filtered. The yellow solid collected was washed with copious amounts of ice-cold water and then dried under high vacuum to afford Preparation 50A (1.96 g, 8 mmol, 77% yield) as a pale yellow solid. ESI MS (M+H)$^+$=246.06. HPLC peak $t_r$=1.912 minutes. HPLC conditions: PHENOMENEX® column, 2.0×50 mm. 4 min. gradient (0-100% B), 0.8 mL/min., 40° C. @ 254 nm; Solvent A: 0.1% TFA in 10% MeOH-90% H$_2$O; Solvent B: 0.1% TFA in 90% MeOH-10% H$_2$O.

Preparation 50B: 7-Iodo-3(2,2,2-trifluoroethyl)-3H-imidazo[4,5-b]pyridine

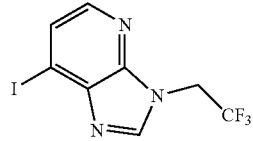

(50B)

To a solution of Preparation 50A (0.75 g, 3.06 mmol) in DMSO (21.86 mL) was added cesium carbonate (2.493 g, 7.65 mmol), followed by 2,2,2-trifluoroethyl trifluoromethanesulfonate (0.463 mL, 3.21 mmol). After stirring the reaction mixture at room temperature for 16 h, the reaction was quenched with water and diluted with EtOAc. The layers were separated and the aqueous layer was extracted with EtOAc (3×). The combined organic phases were washed with brine, dried over Na$_2$SO$_4$, filtered, and concentrated to afford a pale yellow oil. The crude material was dissolved in a minimal amount of CH$_2$Cl$_2$ and chromatographed. Purification of the crude material by silica gel chromatography using a BIOTAGE® machine (eluent 30% EtOAc in hexanes) afforded Preparation 50B as a white solid (0.621 g, 1.899 mmol, 62% yield). ESI MS (M+H)$^+$=327.97. HPLC peak t$_r$=3.071 minutes. HPLC conditions: PHENOMENEX® column, 2.0×50 mm. 4 min. gradient (0-100% B), 0.8 mL/min., 40° C. @ 220 nm; Solvent A: 0.1% TFA in 10% MeOH-90% H$_2$O; Solvent B: 0.1% TFA in 90% MeOH-10% H$_2$O.

Example 50

A pressure vessel was charged with a mixture of dichloro[1,1'bis(diphenylphosphino)ferrocene]palladium(II) dichloromethane adduct (0.05 g, 0.061 mmol), Preparation 50B (0.4 g, 1.223 mmol), potassium phosphate tribasic (0.779 g, 3.67 mmol) and 4-methylpyridin-3-ylboronic acid (0.251 g, 1.835 mmol) under a nitrogen atmosphere. To this mixture were added 1,4-dioxane (4.7 mL) and water (1.835 mL) and the resulting mixture was degassed for 2 min, then heated at 85° C. in an oil bath for 16 h. The reaction mixture was cooled to room temperature and filtered. The filter cake was rinsed with copious amounts of MeOH. The filtrate was concentrated under reduced pressure. The crude material was taken up in MeOH and purified by preparative HPLC using PHENOMENEX®-Luna column eluting with aqueous MeOH containing 0.1% TFA, gradient 25 to 95%, gradient time 14 min. Concentration of the appropriate fractions provided Example 50 as a TFA. The salt was adsorbed onto a 1 g MCX cartridge, followed by elution with 2M solution of ammonia in methanol (30 mL). Evaporation of the solvent under reduced pressure provided the title compound (0.133 g, 36.8% yield) as the free base. $^1$H NMR (400 MHz, MeOD) δ ppm 8.95 (1H, s), 8.85 (1H, d, J=6.02 Hz), 8.68 (1H, d, J=5.02 Hz), 8.64 (1H, s), 8.15 (1H, d, J=6.27 Hz), 7.54 (1H, d, J=5.02 Hz), 5.29 (2H, q, J=9.03 Hz), 2.60 (3H, s). ESI MS (M+H)$^+$=293.13. HPLC peak t$_r$=2.015 minutes. Purity=99%; HPLC conditions: PHENOMENEX® column, 2.0×50 mm. 4 min. gradient (0-100% B), 0.8 mL/min., 40° C. @ 220 nm; Solvent A: 0.1% TFA in 10% MeOH-90% H$_2$O; Solvent B: 0.1% TFA in 90% MeOH-10% H$_2$O.

Biological Assays

The pharmacological properties of the compounds of this invention may be confirmed by a number of biological assays. The exemplified biological assays, which follow, have been carried out with compounds of the invention and/or salts thereof.

CYP17 Total SPA Assay

The assays were performed in U-bottom 384-well optiplates. The final assay volume was 15 µl prepared from 7.5 µl additions of microsomes (prepared as a high-speed pellet from homogenized HEK2 cells stably transfected with CYP17), substrates (3H-Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 µl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a TOPCOUNT® (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

Table 3 below lists the IC$_{50}$ values for the following examples of this invention measured in the Total CYP17 SPA Assay hereinabove. The compounds of the present invention, as exemplified by the following examples, showed Human CYP17 SPA IC$_{50}$ values of less than 1 µM.

TABLE 3

Human CYP17 Inhibition

| Example | SPA IC$_{50}$ (nM) |
|---|---|
| 2 | 5.8 |
| 4 | 37 |
| 6 | 250 |
| 9 | 40 |
| 14 | 11 |
| 15 | 758 |
| 29 | 656 |
| 30 | 405 |
| 31 | 12 |
| 35 | 330 |
| 37 | 396 |
| 39 | 361 |
| 44 | 674 |
| 45 | 135 |
| 46 | 797 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (Cal-Biochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and IC$_{50}$ values.

Cyp17 Hydroxylase Assay

E. coli was transformed to express active human CYP17 and membranes prepared from the transformed E. coli were used as the source of enzyme. The reaction was carried out in a 50 µL final volume containing 200 nM hCYP17 membranes, 25 µM Pregnenolone (Sigma), 7 mM NADPH (Cal-Biochem), 1 µM cytochrome P450 reductase (Invitrogen), and 50 mM sodium phosphate buffer, pH 7.3. The IC$_{50}$ determination of compounds dissolved in 100% DMSO was done by serial dilution into the assay buffer to a final concentration of 0.2% DMSO. The reaction was incubated at 37° C. for 120 minutes and stopped by the addition of 200 µL of 0.02N HCl in acetonitrile. Samples were then spun at 750000 g and 200 µL of the supernatant was transferred to a clean tube for analysis. The product of the reaction, 17 alpha pregnenolone, was measured via LC/MS.

Cyp17 HEK293 Cell Based Assay

HEK293 cells were stably transfected with human Cyp17 and individual clones analyzed for Cyp17 enzymatic activity via LC/MS. A single clone showing robust activity was selected and scaled up. Cells were seeded in 96 well plates and a serial dilution of compounds dissolved in DMSO was added to the cells. Following an incubation of 4 hours, reactions were neutralized by the addition of 200 ul of acetonitrile containing 0.5 uM pregnenolone as tracer. Plates were spun down at 2K for 15 minutes and supernatants transferred to siliconized 96 well plates. The end product of the reaction DHEA was analyzed via LC/MS.

1-Day Cyno PK/PD Study Protocol

Animals: All procedures involving animals and their care were conducted in conformity with the guidelines that are in compliance with the Bristol-Myers Squibb Institutional Animal Care and Use Committee. Fully mature male cynomolgus monkeys (>4 yrs of age; 5-6 kg) were from an in-house colony. All the monkeys used had chronically implanted femoral vein access ports. For oral studies, all animals were fasted overnight prior to dosing and were fed 4 hr after dosing. All animals had free access to water and were conscious throughout the study.

Drug: For all oral pharmacokinetic studies in cynomolgus monkeys, the tested compound was formulated in polyethylene glycol (PEG 400): water (80:20, v:v) at concentrations of 1-5 mg/mL.

Drug Treatment: The tested compound was administered by oral gavage to cynomolgus monkeys.

Sampling: Blood samples were collected from the femoral port, at 15, 30, and 45 min, and 1, 2, 4, 6, 8, 12, 24, 30, and 48 hr after oral administration. All blood samples were collected into syringes containing sodium heparin. The plasma fraction was immediately separated by centrifugation (14,000 rpm, 10 min, 4° C.), frozen on dry ice, and stored at −20° C. until the samples were analyzed.

Analysis of Tested Compound: Plasma samples were thawed and treated with two volumes of acetonitrile containing internal standard. After centrifugation to remove precipitated proteins, an aliquot of supernatant was analyzed by LC/MS/MS.

Analysis of Steroids: Plasma samples were thawed, and assayed in accordance with package insert instructions for the following kits: Coat-A-Count total testosterone solid phase RIA kit, Coat-A-Count total progesterone solid phase RIA kit, and Coat-A-Count total cortisol solid phase RIA kit (Diagnostic Product Corp, Siemens Healthcare Diagnostics, Deerfield, Ill.).

FIG. 1 shows the results of a 1-day PK/PD study in NHP cynomolgus monkeys with Example 31. Example 31 was formulated in 80% PEG-400/water at a volume of 1 mL/kg of monkey and administered orally at 2 mg/kg. The formulation was then dosed orally at time=0 hours and blood samples were taken over a 24 hour period to monitor for drug exposure and testosterone levels. As shown in FIG. 1, testosterone levels were reduced to ~15 ng/dL after a single oral dose of Example 31, consistent with an inhibitor of CYP17 lyase.

What is claimed is:

1. A compound of Formula (I)

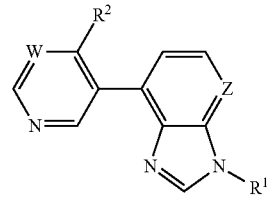

or pharmaceutically acceptable salts thereof, wherein:

Z is CH or N;

W is $CR^3$ or N;

$R^1$ is:
  (i) $C_{1-4}$alkyl substituted with zero to 4 $R^a$;
  (ii) $C_{3-6}$ cycloalkyl substituted with zero to 2 $R^a$;
  (iii) $-S(O)_2(C_{1-3}alkyl)$, $-S(O)_2(C_{1-2}fluoroalkyl)$, or $-C(O)(C_{1-4}alkyl)$;
  (iv) phenyl or naphthalenyl substituted with zero to 4 $R^b$; or
  (v) 1- or 2-ring heteroaryl comprising at least nitrogen heteroatom, substituted with zero to 4 $R^c$;

$R^2$ is:
  (i) H, F, Cl, $-OR^d$, $-NHR^e$, or $-C(O)O(C_{1-4}alkyl)$;
  (ii) $C_{1-4}$alkyl substituted with zero to 4 $R^a$; or
  (iii) $C_{3-6}$ cycloalkyl;

$R^3$ is:
  (i) H, F, Cl, $-CN$, $-OR^d$, $-NHR^e$, $-C(O)O(C_{1-4}alkyl)$; or
  (ii) $C_{1-4}$alkyl substituted with zero to 4 $R^a$;

or $R^2$ and $R^3$ can be combined to form:
  (i) a 5- to 6-membered aryl fused radical substituted with zero to 1 $R^a$; or
  (ii) a 5- to 6-membered heteroaryl fused radical comprising one heteroatom, wherein said heteroaryl fused radical is substituted with zero to 1 $R^a$;

each $R^a$ is independently F, Cl, $-OH$, $-CN$, $C_{3-6}$cycloalkyl, $C_{1-2}$fluoroalkyl, $C_{1-2}$fluoroalkoxy, and/or phenyl substituted with zero to 4 $R^b$;

each $R^b$ is independently F, Cl, Br, $-OH$, $-CN$, $C_{1-4}$alkyl, $C_{3-6}$cycloalkyl, $C_{1-2}$fluoroalkyl, $C_{1-2}$alkoxy, $C_{1-2}$fluoroalkoxy, $-NH_2$, $-NH(CH_3)$, $-N(CH_3)_2$, $-C(O)OH$, $-S(O)_2(C_{1-4}alkyl)$, and/or $-S(O)_2NR^fR^f$;

each $R^c$ is independently F, Cl, Br, $-CN$, $-OH$, $C_{1-4}$alkyl, $C_{3-6}$cycloalkyl, $C_{1-2}$fluoroalkyl, $C_{1-2}$alkoxy, $C_{1-2}$fluoroalkoxy, $-NH_2$, $-NH(CH_3)$, and/or $-N(CH_3)_2$;

$R^d$ is $C_{1-4}$alkyl substituted with zero to 4 $R^a$;

each $R^e$ is independently H and/or $C_{1-4}$alkyl substituted with zero to 4 $R^a$;

and each $R^f$ is independently H, $C_{1-6}$alkyl, $C_{3-6}$cycloalkyl, $C_{1-4}$fluoroalkyl, and/or aryl.

2. The compound according to claim 1 or pharmaceutically acceptable salts thereof, wherein:

$R^1$ is:
  (i) $C_{1-4}$alkyl substituted with zero to 3 $R^a$;
  (ii) $C_{3-6}$ cycloalkyl;
  (iii) $-S(O)_2(C_{1-3}alkyl)$, $-S(O)_2(C_{1-2}fluoroalkyl)$, or $-C(O)(C_{1-4}alkyl)$;
  (iv) phenyl substituted with zero to 4 $R^b$; or
  (v) thiazolyl, pyridinyl, pyridazinyl, pyrimidinyl, pyrazinyl, benzothiazolyl, or isoquinolinyl substituted with zero to 3 $R^c$;

$R^2$ is:
 (i) H, Cl, $C_{1-2}$alkoxy, —NHR$^e$, or —C(O)OCH$_3$; or
 (ii) —CH$_3$, —CF$_3$, —CH$_2$OH, —CHCl$_2$, or —CH$_2$CN;
$R^3$ is H;
or $R^2$ and $R^3$ can be combined to form 6-membered aryl fused radical;
each $R^a$ is independently F, —OH, —CN, —CF$_3$, and/or phenyl substituted with zero to 2 $R^b$;
each $R^b$ is independently F, Cl, Br, —CN, $C_{1-3}$alkyl, —CF$_3$, $C_{1-2}$alkoxy, —OCF$_3$, —C(O)OH, and/or —S(O)$_2$NH$_2$;
each $R^c$ is independently F, Cl, Br, —CN, —OH, $C_{1-3}$alkyl, —CF$_3$, and/or $C_{1-2}$alkoxy; and
$R^e$ is H or $C_{1-2}$fluoroalkyl.

3. The compound according to claim 2 or pharmaceutically acceptable salt thereof,
wherein:
$R^1$ is:
 (i) —CH$_2$CN, or —CH$_2$CH$_2$F, —CH$_2$CF$_3$, or —CH$_2$(phenyl);
 (ii) cyclopropyl;
 (iii) —S(O)$_2$(CH$_2$CH$_3$) or —C(O)CH(CH$_3$)$_2$; or
 (iv) phenyl, thiazolyl, pyridinyl, pyridazinyl, pyrimidinyl, or pyrazinyl substituted with zero to 2 substituents independently selected from F, Cl, —CN, —CH$_3$, —CF$_3$, and/or —OCH$_3$; or
 (iv) benzothiazolyl or isoquinolinyl; and
$R^2$ is Cl, —CH$_3$, —CH$_2$OH, $C_{1-2}$alkoxy, or —NH$_2$;
$R^3$ is H;
or $R^2$ and $R^3$ can be combined to form 6-membered aryl fused radical.

4. The compound according to claim 3 or pharmaceutically acceptable salt thereof, wherein: W is CH.

5. The compound according to claim 1 or pharmaceutically acceptable salt thereof, wherein said compound is selected from 4-(4-methylpyridin-3-yl)-1-phenyl-1H-benzo[d]imidazole (1); 4-(4-methylpyridin-3-yl)-1-(pyridin-2-yl)-1H-benzo[d]imidazole (2); 4-(4-(4-methylpyridin-3-yl)-1H-benzo[d]imidazol-1-yl)thiazole (3); 4-(4-methylpyridin-3-yl)-1-(pyrazin-2-yl)-1H-benzo[d]imidazole (4); 2-(4-(4-methylpyridin-3-yl)-1H-benzo[d]imidazol-1-yl)thiazole (5); 4-(4-methylpyridin-3-yl)-1-(pyridazin-3-yl)-1H-benzo[d]imidazole (6); 2-(4-(4-methylpyridin-3-yl)-1H-benzo[d]imidazol-1-yl)benzonitrile (7); 4-(4-methylpyridin-3-yl)-1-(pyrimidin-5-yl)-1H-benzo[d]imidazole (8); 4-(4-methylpyridin-3-yl)-1-(6-(trifluoromethyl)pyridin-2-yl)-1H-benzo[d]imidazole (9); 4-(4-methylpyridin-3-yl)-1-(4-(trifluoromethyl)pyridin-2-yl)-1H-benzo[d]imidazole (10); 4-(4-methylpyridin-3-yl)-1-(3-(trifluoromethyl)pyridin-2-yl)-1H-benzo[d]imidazole (11); 1-(3-methoxypyridin-2-yl)-4-(4-methylpyridin-3-yl)-1H-benzo[d]imidazole (12); 1-(5-fluoropyridin-2-yl)-4-(4-methylpyridin-3-yl)-1H-benzo[d]imidazole (13); 1-(6-fluoropyridin-2-yl)-4-(4-methylpyridin-3-yl)-1H-benzo[d]imidazole (14); 1-(3,5-difluoropyridin-2-yl)-4-(4-methylpyridin-3-yl)-1H-benzo[d]imidazole (15); 1-(4-fluorophenyl)-4-(4-methylpyridin-3-yl)-1H-benzo[d]imidazole (16); 4-(4-methylpyridin-3-yl)-1-(pyridin-3-yl)-1H-benzo[d]imidazole (17); 1-(6-chloropyridin-2-yl)-4-(4-methylpyridin-3-yl)-1H-benzo[d]imidazole (18); 2-(4-(4-methylpyridin-3-yl)-1H-benzo[d]imidazol-1-yl)nicotinonitrile (19); 2-(4-(4-methylpyridin-3-yl)-1H-benzo[d]imidazol-1-yl)quinoline (20); 2-(4-(4-methylpyridin-3-yl)-1H-benzo[d]imidazol-1-yl)benzo[d]thiazole (21); 1-(2-methoxypyridin-3-yl)-4-(4-methylpyridin-3-yl)-1H-benzo[d]imidazole (22); 1-(3-chloropyridin-2-yl)-4-(4-methylpyridin-3-yl)-1H-benzo[d]imidazole (23); 1-(5-fluoropyridin-3-yl)-4-(4-methylpyridin-3-yl)-1H-benzo[d]imidazole (24); 1-(3-fluoropyridin-2-yl)-4-(4-methylpyridin-3-yl)-1H-benzo[d]imidazole (25); 4-methyl-2-(4-(4-methylpyridin-3-yl)-1H-benzo[d]imidazol-1-yl)thiazole (26); 4-(4-methylpyridin-3-yl)-1-(4-(trifluoromethyl)pyridin-3-yl)-1H-benzo[d]imidazole (27); 5-methyl-2-(4-(4-methylpyridin-3-yl)-1H-benzo[d]imidazol-1-yl)thiazole (28); 4-(4-methylpyridin-3-yl)-1-(pyrimidin-4-yl)-1H-benzo[d]imidazole (29); 4-(4-methylpyridin-3-yl)-1-(pyridin-4-yl)-1H-benzo[d]imidazole (30); 4-(4-methylpyridin-3-yl)-1-(2,2,2-trifluoroethyl)-1H-benzo[d]imidazole (31); 1-benzyl-4-(4-methylpyridin-3-yl)-1H-benzo[d]imidazole (32); 1-(ethylsulfonyl)-4-(4-methylpyridin-3-yl)-1H-benzo[d]imidazole (33); 2-methyl-1-(4-(4-methylpyridin-3-yl)-1H-benzo[d]imidazol-1-yl)propan-1-one (34); 2-(4-(4-methylpyridin-3-yl)-1H-benzo[d]imidazol-1-yl)acetonitrile (35); 1-(2-fluoroethyl)-4-(4-methylpyridin-3-yl)-1H-benzo[d]imidazole (36); 1-cyclopropyl-4-(4-methylpyridin-3-yl)-1H-benzo[d]imidazole (37); (3-(1-(2,2,2-trifluoroethyl)-1H-benzo[d]imidazol-4-yl)pyridin-4-yl)methanol (38); 4-(4-chloropyridin-3-yl)-1-(2,2,2-trifluoroethyl)-1H-benzo[d]imidazole (39); 4-(4-chloropyridin-3-yl)-1-(ethylsulfonyl)-1H-benzo[d]imidazole (40); 4-(4-methoxypyridin-3-yl)-1-(2,2,2-trifluoroethyl)-1H-benzo[d]imidazole (41); 1-(ethylsulfonyl)-4-(4-methoxypyridin-3-yl)-1H-benzo[d]imidazole (42); 4-(4-methylpyrimidin-5-yl)-1-(pyridin-2-yl)-1H-benzo[d]imidazole (43); 5-(1-(2,2,2-trifluoroethyl)-1H-benzo[d]imidazol-4-yl)pyrimidin-4-amine (44); 4-(4-ethoxypyrimidin-5-yl)-1-(2,2,2-trifluoroethyl)-1H-benzo[d]imidazole (45); 5-(1-(2,4-difluorophenyl)-1H-benzo[d]imidazol-4-yl)pyrimidin-4-amine (46); 5-(1-(4-fluorophenyl)-1H-benzo[d]imidazol-4-yl)pyrimidin-4-amine (47); 4-(1-(6-fluoropyridin-2-yl)-1H-benzo[d]imidazol-4-yl)isoquinoline (48); 4-(1-(pyridin-2-yl)-1H-benzo[d]imidazol-4-yl) isoquinoline (49); and 7-(4-methylpyridin-3-yl)-3-(2,2,2-trifluoroethyl)-3H-imidazo[4,5-b]pyridine (50).

6. A pharmaceutical composition, comprising; a pharmaceutically acceptable carrier and a compound according to claim 1 or pharmaceutically acceptable salts thereof.

* * * * *

UNITED STATES PATENT AND TRADEMARK OFFICE
CERTIFICATE OF CORRECTION

PATENT NO. : 9,133,160 B2  
APPLICATION NO. : 13/876646  
DATED : September 15, 2015  
INVENTOR(S) : Audris Huang et al.

Page 1 of 1

It is certified that error appears in the above-identified patent and that said Letters Patent is hereby corrected as shown below:

Title Page

Col. 1, item (73) (Assignee), line 1, delete "Bristol-Meyers" and insert -- Bristol-Myers --, therefor.

Col. 2, item (56) (Other Publications), line 3, delete "nitrophyridine, Boorganic" and insert -- nitropyridine, Bioorganic --, therefor.

Signed and Sealed this  
Tenth Day of May, 2016

Michelle K. Lee  
*Director of the United States Patent and Trademark Office*